US010620037B2

(12) United States Patent
Bauer et al.

(10) Patent No.: US 10,620,037 B2
(45) Date of Patent: Apr. 14, 2020

(54) OBTAINING TRUE DIFFUSIVITY CONSTANT

(71) Applicant: Ventana Medical Systems, Inc., Tucson, AZ (US)

(72) Inventors: Daniel Bauer, Tucson, AZ (US); Michael Otter, Tucson, AZ (US); Benjamin Stevens, Oro Valley, AZ (US)

(73) Assignee: Ventana Medical Systems, Inc., Tucson, AZ (US)

( * ) Notice: Subject to any disclaimer, the term of this patent is extended or adjusted under 35 U.S.C. 154(b) by 341 days.

(21) Appl. No.: 15/624,644

(22) Filed: Jun. 15, 2017

(65) Prior Publication Data

US 2017/0284859 A1 Oct. 5, 2017

Related U.S. Application Data

(63) Continuation of application No. PCT/EP2015/080251, filed on Dec. 17, 2015.
(Continued)

(51) Int. Cl.
*G01H 5/00* (2006.01)
*G01N 29/07* (2006.01)
(Continued)

(52) U.S. Cl.
CPC .............. *G01H 5/00* (2013.01); *A61B 8/4483* (2013.01); *G01N 29/024* (2013.01); *G01N 29/07* (2013.01);
(Continued)

(58) Field of Classification Search
CPC .......... G01N 2291/02441; G01N 2291/02475; G01N 29/00; A61B 8/00; G01H 5/00
See application file for complete search history.

(56) References Cited

U.S. PATENT DOCUMENTS

| 7,262,022 B2 * | 8/2007 | Chu | G01N 1/30 422/127 |
| 2012/0003664 A1 * | 1/2012 | Lovborg | G01N 1/31 435/7.1 |

(Continued)

FOREIGN PATENT DOCUMENTS

| DE | 10146323 A1 | 4/2003 |
| FR | 2987128 A1 | 8/2013 |

(Continued)

OTHER PUBLICATIONS

Coutelieris, Frank A., and J. M. P. Q. Delgado. "Experimental and Numerical Investigation of Mass Transport in Porous Media." Transport Processes in Porous Media. Springer, Berlin, Heidelberg, 2012. 123-173. (Year: 2012).*

(Continued)

*Primary Examiner* — Omar F Fernandez Rivas
*Assistant Examiner* — David A Hopkins
(74) *Attorney, Agent, or Firm* — Charney IP Law LLC; Thomas M. Finetti

(57) ABSTRACT

The subject disclosure presents systems and computer-implemented methods for calculating the diffusivity constant of a sample using acoustic time-of-flight (TOF) based information correlated with a diffusion model to reconstruct a sample's diffusivity coefficient. Operations disclosed herein such as acoustically determining the phase differential accumulated through passive fluid exchange (i.e. diffusion) based on the geometry of the tissue sample, modeling the impact of the diffusion on the TOF, and using a post-processing algorithm to correlate the results to determine the diffusivity constant, are enabled by monitoring the changes in the speed of sound caused by penetration of fixative such as formalin into several tissue samples. A tissue preparation system may be adapted to monitor said diffusion of a tissue sample and determine an optimal processing workflow.

27 Claims, 13 Drawing Sheets

Related U.S. Application Data

(60) Provisional application No. 62/093,151, filed on Dec. 17, 2014.

(51) Int. Cl.
| | |
|---|---|
| *G01N 29/44* | (2006.01) |
| *G01N 29/024* | (2006.01) |
| *A61B 8/00* | (2006.01) |
| *A61B 5/06* | (2006.01) |
| *A61N 7/00* | (2006.01) |

(52) U.S. Cl.
CPC .......... *G01N 29/4472* (2013.01); *A61B 5/066* (2013.01); *A61N 2007/0039* (2013.01); *G01N 2291/0245* (2013.01); *G01N 2291/02475* (2013.01)

(56) References Cited

U.S. PATENT DOCUMENTS

| | | | |
|---|---|---|---|
| 2013/0224791 A1* | 8/2013 | Taft | G01N 1/30 435/40.52 |
| 2015/0033862 A1 | 2/2015 | Bois et al. | |
| 2015/0120255 A1* | 4/2015 | King | E21B 43/00 703/2 |

FOREIGN PATENT DOCUMENTS

| | | |
|---|---|---|
| JP | 59162450 A | 9/1984 |
| JP | 2010037812 A | 2/2010 |
| JP | 2013521506 A | 6/2013 |
| JP | 2014505890 A | 3/2014 |
| WO | 2011109769 A1 | 9/2011 |
| WO | 2012110646 A1 | 8/2012 |
| WO | WO2013124588 A1 | 8/2013 |

OTHER PUBLICATIONS

Baldwin, Steven L., et al. "Measurements of the anisotropy of ultrasonic velocity in freshly excised and formalin-fixed myocardial tissue." The Journal of the Acoustical Society of America 118.1 (2005): 505-513. (Year: 2005).*
Wydra, Adrian. "Development of a new forming process to fabricate a wide range of phantoms that highly match the acoustical properties of human bone." (2013). (Year: 2013).*
Kapellos, George E., Terpsichori S. Alexiou, and Alkiviades C. Payatakes. "A multiscale theoretical model for diffusive mass transfer in cellular biological media." Mathematical biosciences 210.1 (2007): 177-237. (Year: 2007).*
Kapellos, George E., and Terpsichori S. Alexiou. "Modeling momentum and mass transport in cellular biological media: From the molecular to the tissue scale." Transport in Biological Media; Becker, SM, Kuznetsov, AV, Eds (2013): 1-40. (Year: 2013).*
Cussler, Edward Lansing. Diffusion: mass transfer in fluid systems. Cambridge university press, 2009. (Year: 2009).*
Harker, A. H., and J. A. G. Temple. "Velocity and attenuation of ultrasound in suspensions of particles in fluids." Journal of Physics D: Applied Physics 21.11 (1988): 1576. (Year: 1988).*
Zaknoune, A., Patrick Glouannec, and Patrick Salagnac. "Estimation of moisture transport coefficients in porous materials using experimental drying kinetics." Heat and Mass Transfer 48.2 (2012): 205-215. (Year: 2012).*
Thomas, Edward V. "A primer on multivariate calibration." Analytical Chemistry 66.15 (1994): 795A-804A. (Year: 1994).*
Sanabria, Sergio J., Marga B. Rominger, and Orcun Goksel. "Speed-of-sound imaging based on reflector delineation." IEEE Transactions on Biomedical Engineering (2018). (Year: 2017).*
Chiarelli, Piero, et al. "Poroelastic longitudinal wave equation for soft living tissues." Journal of Biorheology 28.1 (2014): 29-37. (Year: 2014).*
International Preliminary Report dated Jun. 20, 2017 in Application No. PCT/EP2015/080251, 7 pages.
International Search Report dated Mar. 30, 2016 in Application No. PCT/EP2015/080251, 12 pages.

* cited by examiner

OBTAINING TRUE DIFFUSIVITY CONSTANT

CROSS-REFERENCE TO RELATED APPLICATIONS

This is a continuation of International Patent Application No. PCT/EP2015/080251 filed Dec. 17, 2015, which claims priority to and the benefit of U.S. Provisional Patent Application No. 62/093,151, filed Dec. 17, 2014, both of which prior applications are incorporated by reference herein.

BACKGROUND OF THE SUBJECT DISCLOSURE

Field of the Subject Disclosure

The present subject disclosure relates to analysis of materials such as tissue samples. More particularly, the present subject disclosure relates to calculating a true diffusivity constant for a material.

Background of the Subject Disclosure

Measuring the diffusivity constant (i.e. diffusivity coefficient) is important to multiple areas of basic and applied science because it represents a fundamental property of fluids and solids and therefore has direct application to a number of commercial fields. For instance, the diagnostic value of the diffusivity coefficient has proven useful in distinguishing normal versus abnormal tissue. In immunohistochemistry (IHC) imaging, biological specimens such as tissue sections from human subjects are often placed in a liquid or fixative that will suspend the metabolic activities of the cells. Monitoring diffusion of fixatives through a tissue sample is useful for determining whether the fixative has infused the entire tissue sample, thereby minimizing or limiting under-fixed tissue or over-fixed tissue.

Several methods for calculating the diffusivity constant have been presented in prior art including magnetic resonance imaging (MRI) diffusion weighted imaging, electrolyte monitoring of a fluid, optical detection and quantification, and x-ray based methods. Of these techniques, MRI-based methods are by far the most common clinically used method. However, each of these methods has its own limitations in terms of detection, sensitivity, cost, complexity, sample compatibility, and required acquisition time. Electrolyte monitoring-based methods require active diffusion of electrically different materials, meaning that electrically-neutral materials cannot be monitored with this method. The major drawback of optical techniques is that they mainly produce a relative representation of the diffusion coefficient that is typically related back to known standard. That can make absolute quantification of the diffusivity constant difficult. As noted earlier, much work has been done using MRI to detect and quantify the diffusivity coefficient. However, this is derived from the detection of the nuclear magnetization of mobile water protons in the body. This makes MRI well-suited to detect and monitor water diffusion although the modality currently has limited utility in monitoring the diffusion of other alternate fluids.

SUMMARY OF THE SUBJECT DISCLOSURE

The subject disclosure solves the above-identified problems by presenting systems and computer-implemented methods for calculating the diffusivity constant of a sample using acoustic time-of-flight (TOF) based information correlated with a diffusion model to reconstruct a sample's diffusivity coefficient. Operations disclosed herein such as acoustically determining the phase differential accumulated through passive fluid exchange (i.e. diffusion) based on the geometry of the tissue sample, modeling the impact of the diffusion on the TOF, and using a post-processing algorithm to correlate the results to determine the diffusivity constant, are enabled by monitoring the changes in the speed of sound caused by penetration of fixative such as formalin into several tissue samples. A tissue preparation system may be adapted to monitor said diffusion of a tissue sample and determine an optimal processing workflow. Moreover, the disclosed operations are not limited to solely quantifying water diffusion, but may be used to monitor the diffusion of all fluids into all tissues and other materials, unlike the prior art methods identified above.

In one exemplary embodiment, the subject disclosure provides a method for determining a true diffusivity constant for a sample immersed within a reagent, the method including simulating a spatial dependence of a diffusion into the sample over a plurality of time points and for each of a plurality of candidate diffusivity constants to generate a model time-of-flight, and comparing the model time-of-flight with an experimental time-of-flight to obtain an error function, wherein a minimum of the error function yields the true diffusivity constant.

In another exemplary embodiment, the subject disclosure provides a system including an acoustic monitoring device that detects acoustic waves that have traveled through a tissue sample, and a computing device communicatively coupled to the acoustic monitoring device, the computing device is configured to evaluate a speed of the acoustic waves based on a time of flight and including instructions, when executed, for causing the processing system to perform operations comprising setting a range of candidate diffusivity constants for the tissue sample, simulating a spatial dependence of a reagent within the tissue sample for a plurality of time points and for a first of the range of candidate diffusivity points, determining a modeled time-of-flight based on the spatial dependence, repeating the spatial dependence simulation for each of the plurality of diffusivity constants, and determining an error between the modeled-time-of-flight for the plurality of diffusivity constants versus an experimental time-of-flight for the tissue sample, wherein a minimum of an error function based on the error yields a true diffusivity constant for the tissue sample.

In yet another exemplary embodiment, the subject disclosure provides a tangible non-transitory computer-readable medium to store computer-readable code that is executed by a processor to perform operations including comparing a simulated time-of-flight for a sample material with an experimental time-of-flight for the sample material, and obtaining a diffusivity constant for the sample material based on a minimum of an error function between the simulated time-of-flight and the acoustic time-of-flight.

BRIEF DESCRIPTION OF THE DRAWINGS

FIG. 11A show reconstructed diffusivity constants for the multiple tissue samples.

DETAILED DESCRIPTION OF THE SUBJECT DISCLOSURE

I. Technical Implementation

Figure 1:
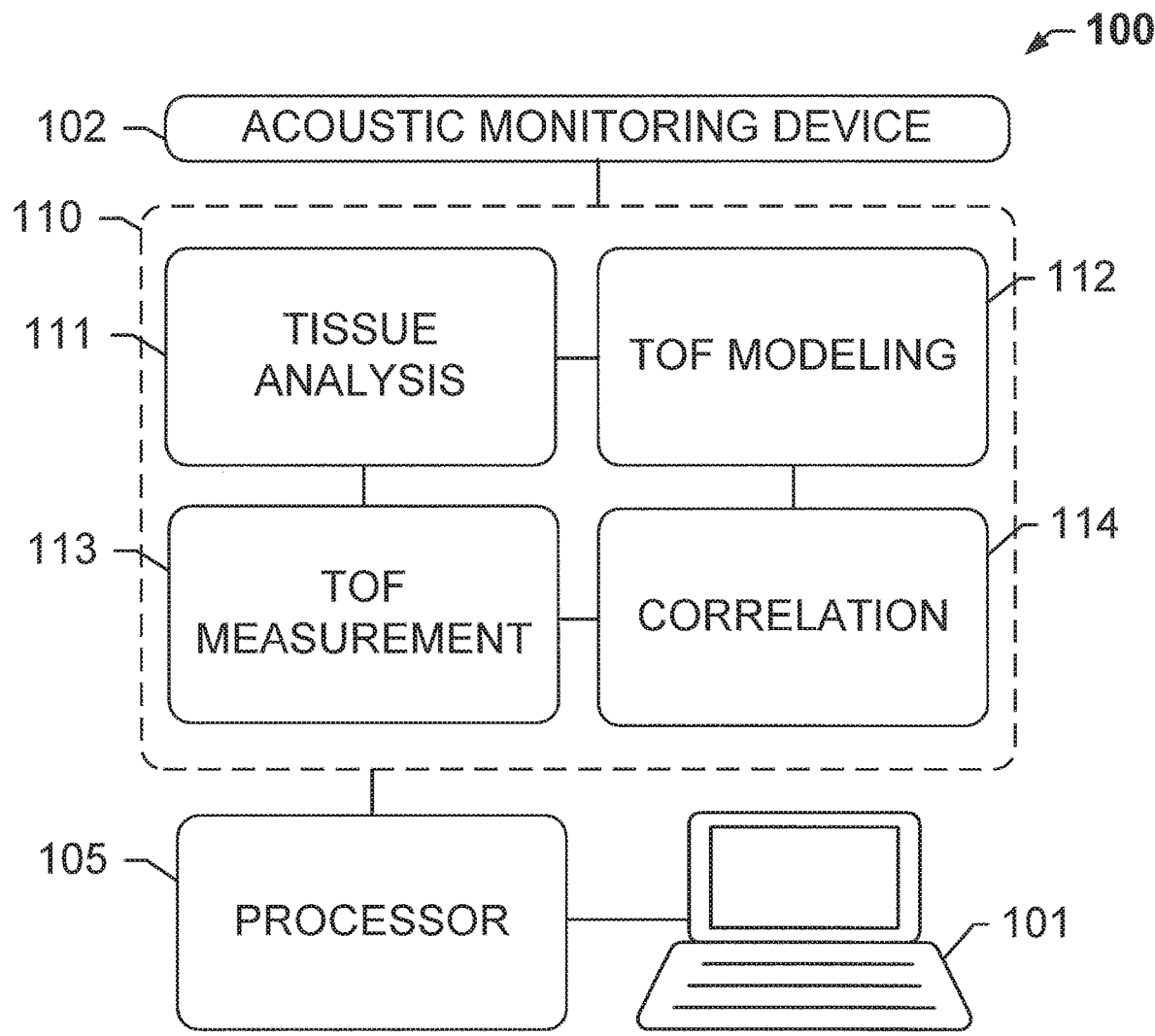
FIG. 1 shows a tissue processing system 100 for optimized tissue fixation, according to an exemplary embodiment of the subject disclosure.

The subject disclosure solves the above-identified problems by presenting systems and computer-implemented methods for calculating the diffusivity constant (also known as "diffusion coefficient") of a sample using acoustic time-of-flight (TOF) based information correlated with a diffusion model to reconstruct a sample's diffusivity coefficient. Tissue preparation systems and methods disclosed herein may be adapted to monitor the diffusion of fixative fluid into a tissue sample. For example, as formalin penetrates into tissue, it displaces interstitial fluid. This fluid exchange slightly changes the composition of the tissue volume because interstitial fluid and formalin have discrete sound velocities. The output ultrasound pulse thus accumulates a small transit time differential that increases as more fluid exchange occurs. This enables operations such as determining the phase differential accumulated by diffusion based on the geometry of the tissue sample, modeling the impact of the diffusion on the TOF, and using a post-processing algorithm to correlate the results to determine the diffusivity constant. Moreover, the sensitivity of the disclosed TOF instruments can detect a change of less than 10 parts per million enabling potentially more accurate characterization of the diffusivity constant. On the nanosecond TOF scale, all fluids and tissues will have discrete sound velocities, so the disclosed operations are not limited to solely quantifying water diffusion, but may be used to monitor the diffusion of all fluids into all tissues.

The rate of diffusion may be monitored by a system of acoustic probes based on the different acoustic properties of formalin-soaked tissue samples. Such a system for diffusion monitoring and experimental TOF measurement is described in further detail in commonly-assigned and co-pending U.S. Patent Publication 2013/0224791, in U.S. patent applications entitled MATERIALS AND METHODS FOR OPTIMIZED TISSUE FIXATION filed in December 2014, in U.S. patent applications entitled MATERIALS AND METHODS FOR STANDARDIZING DIFFUSION OF A FLUID INTO TISSUES filed in Feb. 9, 2015 and in U.S. patent application entitled DIFFUSION MONITORING PROTOCOL FOR OPTIMIZED TISSUE FIXATION filed in Dec. 29, 2014, the contents of each of which are hereby incorporated by reference herein in their entirety. A suitable system for diffusion monitoring and experimental TOF measurement is also described in the international patent application entitled ACCURATELY CALCULATING ACOUSTIC TIME-OF-FLIGHT filed in Dec. 17, 2015, the contents of each of which are hereby incorporated by reference herein in their entirety. The referenced applications describe solid tissue samples being contacted with a liquid fixative that travels through the tissue samples and diffuses throughout substantially the entire thickness of the tissue samples, and being analyzed based on acoustic characteristics that are continuously or periodically monitored to evaluate the state and condition of the tissue sample throughout processing. For example, a fixative such as formalin having a bulk modulus greater than interstitial fluid can significantly alter the ToF as it displaces the interstitial fluid. Based on the obtained information, a fixation protocol may be adjusted to enhance processing consistency, reduce processing times, improve processing quality, or the like. The acoustic measurements may be used to non-invasively analyze tissue samples. The acoustic properties of tissue samples may change as liquid reagent (e.g., a liquid fixative) travels through the sample. The sample's acoustic properties can change during, for example, a pre-soak process (e.g., diffusion of cold fixative), a fixation process, a staining process, or the like. In the fixation process (e.g., a cross-linking process), the speed of transmission of acoustic energy can change as the tissue sample becomes more heavily cross-linked. Real-time monitoring can be used to accurately track movement of the fixative through the sample. For example, a diffusion or fixation status of a biological sample can be monitored based on a time of flight (TOF) of acoustic waves. Other examples of measurements include acoustic signal amplitude, attenuation, scatter, absorption, phase shifts of acoustic waves, or combinations thereof.

According to embodiment, the movement of the fixative through the tissue sample may be monitored in real-time.

II. Systems and Methods

A "time-of-flight" or "TOF" as used herein is, for example, the time that it takes for an object, particle or acoustic, electromagnetic or other wave to travel a distance through a medium. The TOF may be measured empirically e.g. by determining a phase differential between the phases of an acoustic signal emitted by a transmitter ("transmitted signal") and an acoustic signal received by a receiver ("received signal").

A "sample" as used herein is, for example, a biological specimen containing multiple cells. Examples include, but are not limited to, tissue biopsy samples, surgical specimen samples, amniocentesis samples and autopsy material. The samples may be contained e.g. on a tissue sample slide.

The "Porosity" is a measure of the void (i.e. "empty") spaces in a material, and is a fraction of the volume of voids over the total volume of an object, between 0 and 1, or as a percentage between 0 and 100%. A "porous material" as used herein is, for example, a 3D object whose porosity is larger than 0.

A "diffusion coefficient" or "diffusivity constant" as used herein is, for example, a proportionality constant between the molar flux due to molecular diffusion and the gradient in the concentration of the object whose diffusion is observed (or the driving force for diffusion). Diffusivity is encountered e.g. in Fick's law and numerous other equations of physical chemistry. The higher the diffusivity (of one substance with respect to another), the faster they diffuse into each other. Typically, a compound's diffusivity constant is ~10,000× as great in air as in water. Carbon dioxide in air has a diffusivity constant of 16 mm2/s, and in water its diffusivity constant is 0.0016 mm2/s.

A "phase differential" as used herein is, for example, the difference, expressed in degrees or time, between two waves having the same frequency and referenced to the same point in time.

A "biopsy capsule" as used herein is, for example, a container for a biopsy tissue sample. Typically, a biopsy capsule comprises a mesh for holding the sample and letting a liquid reagent, e.g. a buffer, a fixation solution or a staining solution surround and diffuse into a tissue sample. A "cassette" as used herein is, for example, a container for a biopsy capsule. Preferentially, the cassette is designed and shaped such that it can automatically be selected and moved, e.g. raised, relative to the beam path of an ultrasonic transmitter-receiver pair. The movement may be performed for example by a robotic arm or another automated movable component of a device onto which the cassette is loaded.

In an embodiment, a system of calculating a diffusion constant is provided, said system comprising a signal analyzer containing a processor and a memory coupled to the processor, the memory to store computer-executable instructions that, when executed by the processor, cause the processor to perform operations including calculation of a diffusivity constant from a set of acoustic data as discussed in further detail below.

A data input into the signal analyzer is an acoustic data set generated by an acoustic monitoring system, said acoustic data set generated by transmitting an acoustic signal so that the acoustic signal encounters a material of interest, and then detecting the acoustic signal after the acoustic signal has encountered the material of interest. Thus, in a further embodiment, a system is provided comprising a signal analyzer as disclosed herein and an acoustic monitoring system discussed in further detail below. Additionally or alternatively, a system may be provided comprising a signal analyzer as disclosed herein and a non-transitory computer readable medium comprising an acoustic data set obtained from an acoustic monitoring system as disclosed herein. In an embodiment, the acoustic data is generated by frequency sweep transmitted and received by the acoustic monitoring system. As used herein, the term "frequency sweep" shall refer to a series of acoustic waves transmitted through a medium, such that a first set of acoustic waves is emitted through the medium at a fixed frequency for a first fixed duration of time, and subsequent sets of acoustic waves are emitted at fixed frequency intervals for subsequent—preferably equal—durations.

In some embodiments, the system is adapted for monitoring diffusion of a fluid into a porous material. In such an embodiment, a system may be provided comprising: (a) a signal analyzer as discussed herein; (b) an acoustic monitoring system as discussed herein and/or a non-transitory computer readable medium comprising an acoustic data set generated by said acoustic monitoring system; and (c) an apparatus for holding a porous material immersed in a volume of a fluid. In an embodiment, said system is for monitoring diffusion of a fixative into a tissue sample.

According to embodiments, the diffusivity constant is determined for the purpose of characterizing or describing an object, e.g. in the fields of pharmaceutics, ceramics, metallurgy, materials, manufacturing, earth sciences, soil mechanics, manufacturing and/or engineering. For example, the method may be used for monitoring a staining process of an object, e.g. cloth, plastics, ceramics, tissues or others, for monitoring a fixation process, for identifying a material of a particular type, e.g. by comparing the diffusivity constant with known reference diffusivity constant values of known materials or of materials with a known composition.

According to some further embodiments, the identified diffusivity constant is used for classifying a biological sample, e.g. a tissue sample. Said classification result may be used, for example, for identifying the tissue type the sample is derived, for determining if the tissue sample is taken from a tumor or from healthy tissue, or for classifying the tissue samples into different tumor-subtypes. For example, from many tumors, it is known that the tumor cells are clustered in close proximity to each other. Samples derived from some tumor types therefore have a different diffusivity constant than samples of the corresponding healthy tissue. By determining, e.g. in a pre-processing step, the diffusivity constants of a samples taken from different tissue- and/or tumor types, storing the determined diffusivity constants as reference values and comparing the stored reference diffusivity constants with the diffusivity value obtained according to embodiments of the invention, embodiments of the invention may be used for classifying tissue samples.

In an embodiment, an acoustic monitoring system for collecting an acoustic data set is provided, said acoustic monitoring system comprising a transmitter and a receiver, wherein said transmitter and receiver are arranged such that acoustic signals generated by the transmitter are received by the receiver and transformed into a computer-readable signal. In an embodiment, the system comprises an ultrasonic transmitter and an ultrasonic receiver. As used herein, a "transmitter" is a device capable of converting an electrical signal to acoustic energy, and an "ultrasonic transmitter" is a device capable of converting an electrical signal to ultrasonic acoustic energy. As used herein, a "receiver" is a device capable of converting an acoustic wave to an electrical signal, and an "ultrasonic receiver" is a device capable of converting ultrasonic acoustic energy to an electrical signal."

Certain materials useful for generating acoustic energy from electrical signals are also useful for generating electrical signals from acoustic energy. Thus, the transmitter and receiver do not necessarily need to be separate components, although they can be. The transmitter and receiver are arranged such that the receiver detects acoustic waves generated by the transmitter after the transmitted waves have encountered a material of interest. In some embodiments, the receiver is arranged to detect acoustic waves that have been reflected by the material of interest. In other embodiments, the receiver is arranged to detect acoustic waves that have been transmitted through the material of interest.

In an embodiment, the transmitter comprises at least a waveform generator operably linked to a transducer, the waveform generator being configured for generating an electrical signal that is communicated to the transducer, the transducer being configured for converting the electrical signal to an acoustic signal. In certain embodiments, the waveform generator is programmable, such that a user may modify certain parameters of the frequency sweep, including for example: starting and/or ending frequency, the step size between frequencies of the frequency sweep, the number of frequency steps, and/or the duration for which each frequency is transmitted. In other embodiments, the waveform generator is pre-programmed to generate one or more a pre-determined frequency sweep pattern. In other embodiments, the waveform generator may adapted to transmitted both pre-programmed frequency sweeps and customized frequency sweeps. The transmitter may also contain a focusing element, which allows the acoustic energy generated by the transducer to be predictably focused and directed to a specific area.

In operation, the transmitter transmits a frequency sweep through the medium, which is then detected by the receiver and transformed into the acoustic data set to be stored in a non-transitory computer readable storage medium and/or transmitted to the signal analyzer for analysis. Where the acoustic data set includes data representative of a phase difference between the transmitted acoustic waves and the received acoustic waves, the acoustic monitoring system may also include a phase comparator, which generates an electrical signal that corresponds to the phase difference between transmitted and received acoustic waves. Thus, in certain embodiments, the acoustic monitoring system comprises a phase comparator communicatively linked to a transmitter and receiver. Where the output of the phase comparator is an analog signal, the acoustic monitoring system may also include an analog to digital converter for converting the analog output of the phase comparator to a digital signal. The digital signal may then be recorded, for example, on a non-transitory computer readable medium, or may be communicated directly to the signal analyzer for analysis.

A signal analyzer is provided containing a processor and a memory coupled to the processor, the memory to store computer-executable instructions that, when executed by the processor, cause the processor to calculate a diffusivity constant based at least in part on an acoustic data set generated by an acoustic monitoring system as discussed above.

The term "processor" encompasses all kinds of apparatus, devices, and machines for processing data, including by way of example a programmable microprocessor, a computer, a system on a chip, or multiple ones, or combinations, of the foregoing. The apparatus can include special purpose logic circuitry, e.g., an FPGA (field programmable gate array) or an ASIC (application-specific integrated circuit). The apparatus also can include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, subprograms, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., an LCD (liquid crystal display), LED (light emitting diode) display, or OLED (organic light emitting diode) display, for displaying information to the user and a keyboard and a pointing device, e.g., a mouse or a trackball, by which the user can provide input to the computer. In some implementations, a touch screen can be used to display information and receive input from a user. Other kinds of devices can be used to provide for interaction with a user as well; for example, feedback provided to the user can be in any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

The computing system can include any number of clients and servers. A client and server are generally remote from each other and typically interact through a communication network. The relationship of client and server arises by virtue of computer programs running on the respective computers and having a client-server relationship to each other. In some embodiments, a server transmits data (e.g., an HTML page) to a client device (e.g., for purposes of displaying data to and receiving user input from a user interacting with the client device). Data generated at the client device (e.g., a result of the user interaction) can be received from the client device at the server.

In operation, the signal analyzer accepts as an input an acoustic data set recorded from a test material. The acoustic data set is representative of at least a portion of a frequency sweep that is detected after the frequency sweep encounters a material of interest. In some embodiments, the portion of the frequency sweep that is detected constitutes acoustic waves that are reflected by the material of interest. In other embodiments, the portion of the frequency sweep that is detected constitutes acoustic waves that have passed through the material of interest.

FIG. 1 shows an embodiment of a system useful for tissue processing 100 for optimized tissue fixation, according to an exemplary embodiment of the subject disclosure. System 100 comprises an acoustic monitoring device 102 communicatively coupled to a memory 110 for storing a plurality of processing modules or logical instructions that are executed by processor 105 coupled to computer 101. Acoustic monitoring device 102 may comprise the aforementioned acoustic probes including one or more transmitters and one or more receivers. The tissue sample may be immersed in a liquid fixative while the transmitters and receivers communicate to detect time of flight (ToF) of acoustic waves. Processing modules within memory 110 may include logical non-transitory computer-readable instructions for enabling processor 105 to perform operations including a tissue analysis module 111 for receiving information about the tissue block via user input or electronic input and for determining tissue characteristics such as an acoustic velocity of the tissue, a TOF modeling module 112 for simulating a spatial dependence of fixative or reagent concentrations for various times and model diffusion constants to generate a time-varying ("expected" or "modeled") TOF signal and outputting a model decay constant by a TOF measurement module 113 for determining an actual TOF signal of the tissue, computing a spatial average, and generating an experimental decay constant based on tissue characteristics (e.g. cell types, cell densities, cell sizes and effects of sample preparation and/or sample staining) and input from acoustic monitoring device 102, and a correlation module 114 for correlating (e.g. comparing) the experimental and modeled TOF data and determining a true diffusivity constant for the tissue sample based on a minimum of an error function of the correlation. These and other operations performed by these modules may result in an output of quantitative or graphical results to a user operations computer 101. Consequently, although not shown in FIG. 1, computer 101 may also include user input and output devices such as a keyboard, mouse, stylus, and a display/touchscreen.

As described above, the modules include logic that is executed by processor 105. "Logic", as used herein and throughout this disclosure, refers to any information having the form of instruction signals and/or data that may be applied to affect the operation of a processor. Software is one example of such logic. Examples of processors are computer processors (processing units), microprocessors, digital signal processors, controllers and microcontrollers, etc. Logic may be formed from signals stored on a computer-readable medium such as memory 110 that, in an exemplary embodiment, may be a random access memory (RAM), read-only memories (ROM), erasable/electrically erasable programmable read-only memories (EPROMS/EEPROMS), flash memories, etc. Logic may also comprise digital and/or analog hardware circuits, for example, hardware circuits comprising logical AND, OR, XOR, NAND, NOR, and other logical operations. Logic may be formed from combinations of software and hardware. On a network, logic may be programmed on a server, or a complex of servers. A particular logic unit is not limited to a single logical location on the network. Moreover, the modules need not be executed in any specific order. Each module may call another module when needed to be executed.

Acoustic monitoring device 102 may be retrofitted onto a commercial dip-and-dunk tissue processor such as the Lynx II by Electron Microscopy Sciences®. A mechanical head designed using Solidworks® software may be fit around and seal a standard reagent canister. Once sealed, an external vacuum system may initiate to degas the bulk reagent as well as the contents of the cassette, including the tissue. A cassette holder designed for use with either a standard sized histological cassette such as CellSafe 5 by CellPath® or a biopsy capsule such as CellSafe Biopsy Capsules by Cell-Path® for smaller tissue samples may be utilized. Each holder would securely hold the tissue to prevent the sample from slipping during the experiment. The cassette holder may be attached to a vertical translation arm that would slide the cassette holder in one direction. The mechanical head may be designed with two metal brackets on either side of the tissue cassette, with one bracket housing 5 transmitting transducers, and the other bracket housing 5 receiving transducers that are spatially aligned with their respective transmitting transducers. The receiving bracket may also house a pair of transducers oriented orthogonal to the propagation axis of the other transducers. After each acquisition the orthogonal sensors may calculate a reference TOF value to detect spatiotemporal variations in the fluid that has a profound effect on sound velocity. Additionally, at the end of each 2D acquisition, the cassette may be raised up and a second reference acquisition acquired. These reference TOF values may be used to compensate for environmentally-induced fluctuations in the formalin. Environmentally-induced fluctuations in the formalin or any other fixative may be, for example, temperature fluctuations in the container comprising the porous material, vibrations, and others.

Figure 2A:
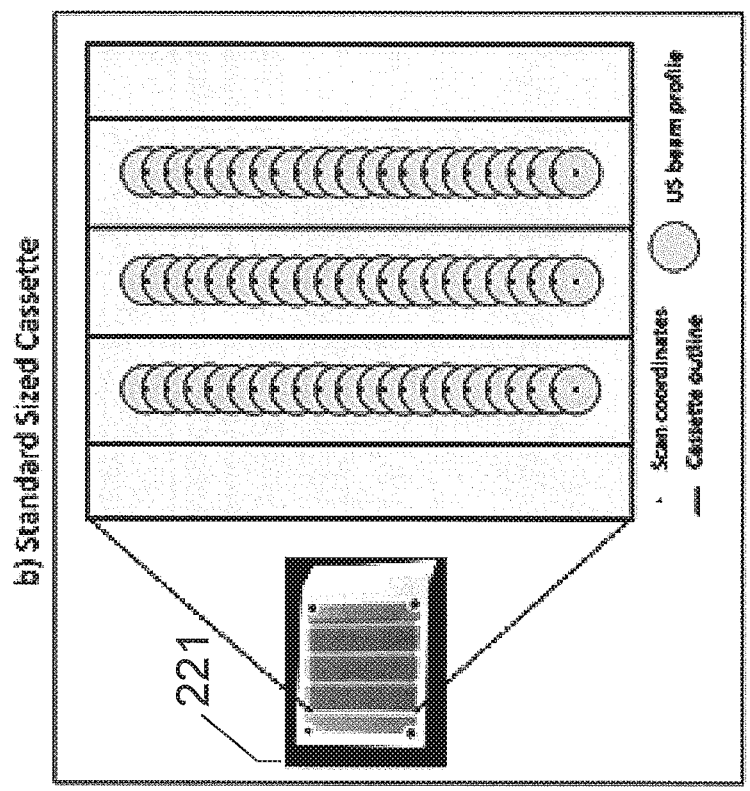
FIGS. 2A and 2B respectively show depictions of ultrasound scan patterns from a biopsy capsule and from a standard-sized cassette, according to an exemplary embodiment of the subject disclosure.
Figure 2B:
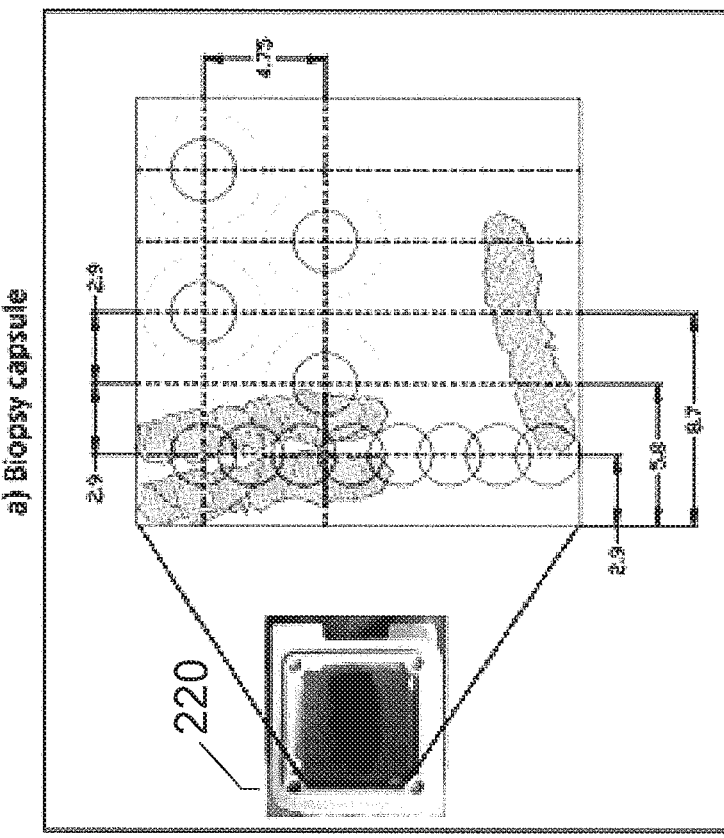

FIGS. 2A and 2B respectively show depictions of ultrasound scan patterns from a biopsy capsule and from a standard-sized cassette, according to an exemplary embodiment of the subject disclosure. The measurement and modeling procedures described in the following for a tissue example may likewise be applied on other forms of porous material, so the tissue sample is only a non-limiting example for a porous material.

As described herein, the measurements from the acoustic sensors in an acoustic monitoring device may be used to track the change and rate of change of a TOF of acoustic signals through the tissue sample. This includes monitoring the tissue sample at different positions over time to determine diffusion over time or a rate of diffusion.

For example, the "different positions", also referred to "candidate diffusivity positions" may be a position within or on the surface of the tissue sample. According to some embodiments, the sample may be positioned at different "sample positions" by a relative movement of biopsy capsule and acoustic beam path. The relative movement may comprise moving the receiver and/or the transducer for "scanning" over the sample in a stepwise or continuous manner. Alternatively, the cassette may be repositioned by means of a movable cassette holder.

For example, to image all the tissue in the cassette, the cassette holder may be sequentially raised ≈1 mm vertically and TOF values acquired at each new position, as depicted in FIGS. 2A and 2B. The process may be repeated to cover the entire open aperture of the cassette. Referring to FIG. 2A, when imaging tissue in the biopsy capsule 220, signals are calculated from all 5 transducers pairs, resulting in the scan pattern depicted in FIG. 2A. Alternatively, when imaging tissue in the standard sized cassette 221 depicted in FIG. 2B, the 2nd and 4th transducer pairs may be turned off and TOF values acquired between the 1st, 3rd, and 5th transducer pairs located at the respective centers of the three middle subdivisions of the standard sized cassette 221. Two tissue cores may then be placed in each column, one on the top and one on the bottom, enabling TOF traces from 6 samples (2 rows×3 columns) to simultaneously be obtained and significantly decreased run to run variation and increased throughput. In this exemplary embodiment, the full-width-half-maximum of the ultrasound beam is 2.2 mm.

Acoustic sensors in the acoustic monitoring device may include pairs of 4 MHz focused transducers such as the TA0040104-10 by CNIRHurricane Tech (Shenzhen) Co., Ltd.® that are spatially aligned, with a tissue sample being placed at their common foci. One transducer, designated the transmitter, may send out an acoustic pulse that traverses the coupling fluid (i.e. formalin) and tissue and is detected by the receiving transducer.

Figure 2C:
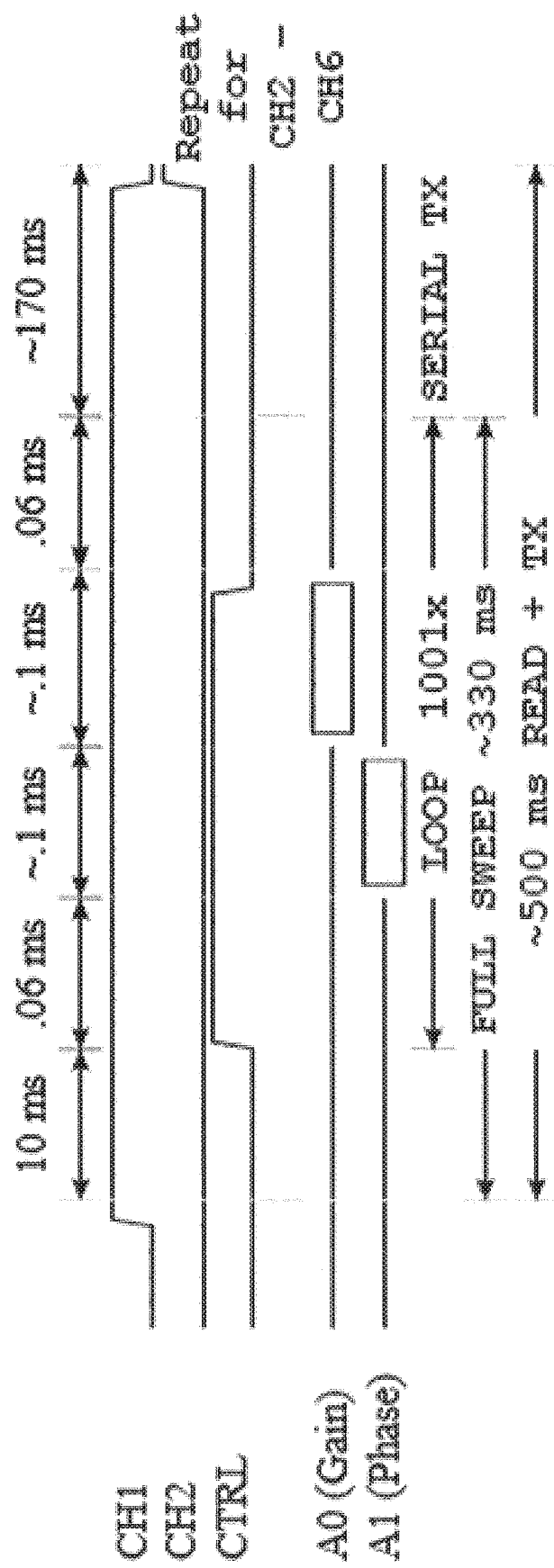
FIG. 2C shows a timing diagram for an exemplary embodiment of the subject disclosure.

FIG. 2C shows a timing diagram for an exemplary embodiment of the subject disclosure. Initially, the transmitting transducer can be programmed with a waveform generator such as the AD5930 by Analog Devices® to transmit a sinusoidal wave for several hundred microseconds. That pulse train may be detected by the receiving transducer after traversing the fluid and tissue. The received ultrasound sinusoid and the transmitted sinusoid may be compared using, for instance, a digital phase comparator such as the AD8302 by Analog Devices. The output of the phase comparator yields a valid reading during the region of temporal overlap between the transmitted and received pulses. The output of the phase comparator is allowed to stabilize before the output is queried with an integrated analog to digital converter on the microcontroller, such as the ATmega2560 by Atmel®. The process may then be repeated at multiple acoustic frequencies across the bandwidth of the transducer to build up the phase relationship between the input and output sinusoids across a frequency range. This acoustic phase-frequency sweep is directly used to calculate the TOF using a post-processing algorithm analogous to acoustic interferometry and capable of detecting transit times with subnanosecond accuracy.

Thus according to embodiments of the invention, the "measured TOF", i.e., the "measured TOF value" obtained for a particular time point and a particular candidate diffusivity point is computed from a measured phase shift between a transmitted ultrasound signal and the corresponding, received ultrasound signal, whereby the beam path of the ultrasound signal crossed the particular candidate diffusivity point and whereby the phase shift was measured at the particular time point.

Figure 3:
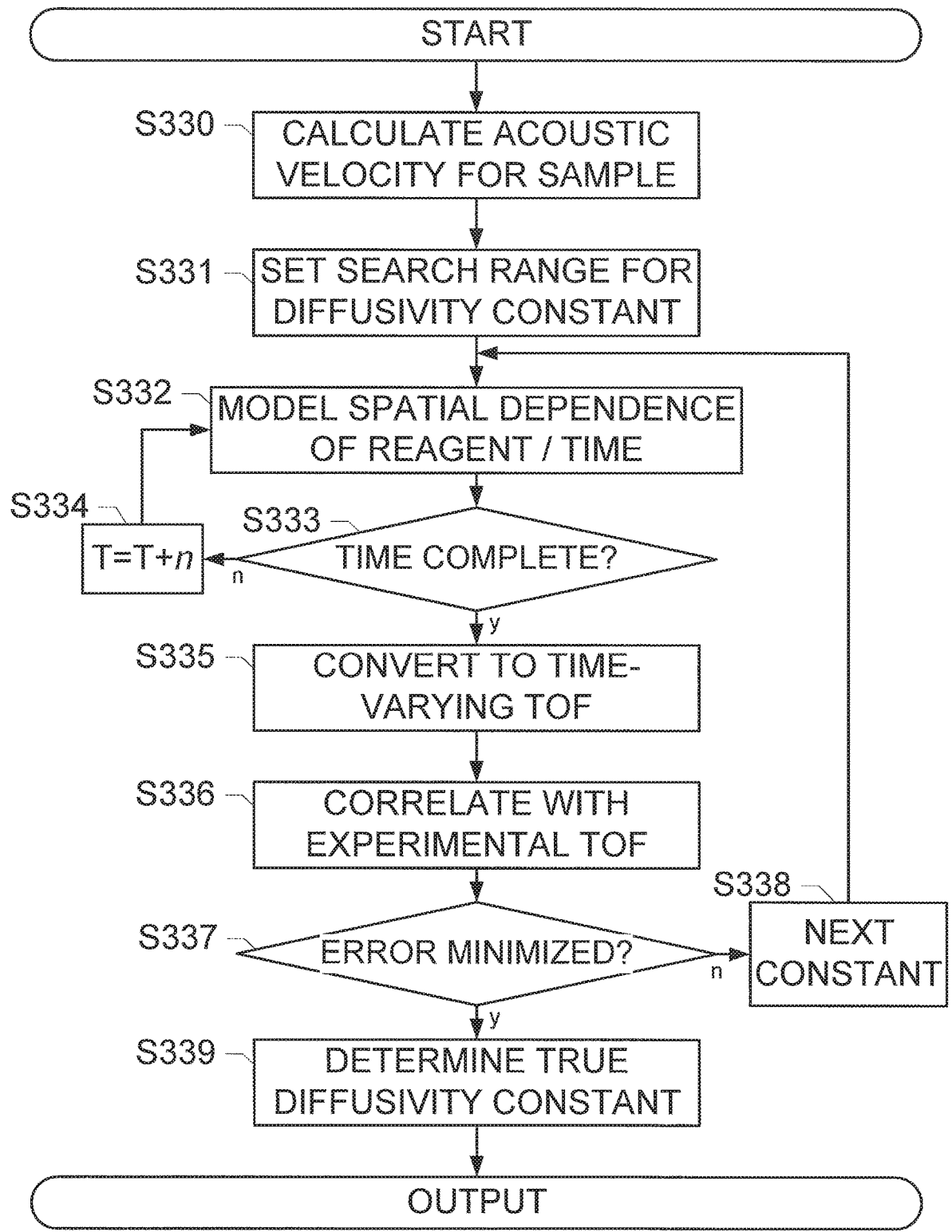
FIG. 3 shows a method for obtaining a diffusivity coefficient for a tissue sample, according to an exemplary embodiment of the subject disclosure.

FIG. 3 shows a method for obtaining a diffusivity coefficient for a tissue sample, according to an exemplary embodiment of the subject disclosure. The operations disclosed with respect to this embodiment may be performed by any electronic or computer-based system, including the system of FIG. 1. These operations may be encoded on a computer-readable medium such as a memory and executed by a processor, resulting in an output that may be presented to a human operator or used in subsequent operations. Moreover, these operations may be performed in any order besides the order disclosed herein, with an understanding of those having ordinary skill in the art, so long as the novel spirit of the subject disclosure is maintained.

The method may include a calculation of an acoustic velocity for the tissue sample (S330). This operation includes calculating a speed of sound in the reagent that the tissue sample is immersed in. For example, a distance between ultrasound transducers $d_{sensor}$ i.e., the distance between the transmitting transducer and the receiving transducer, may be accurately measured, and a transit time $t_{reagent}$ between the ultrasound transmitter and the ultrasound receiver in pure reagent is measured, with the speed of sound in the reagent $r_{reagent}$ being calculated using:

$$r_{reagent} = \frac{d_{sensor}}{t_{reagent}}$$

The tissue thickness may also be obtained via measurement or user input. A variety of suitable techniques are available to obtain tissue thickness, including ultrasound, mechanical, and optical methods. Finally, the acoustic velocity is determined (S330) by obtaining the phase retardation from the undiffused tissue (i.e., a tissue sample to which the fixation solution has not been applied yet) with respect to the bulk reagent (e.g. the fixation solution) using:

$$\Delta t = t_{tissue+reagent} - t_{reagent} \text{ and}$$

$$\frac{1}{r_{tissue}(t=0)} = \frac{1}{r_{reagent}} + \frac{\Delta t}{d_{tissue}}$$

The specific equation is derived based on the known geometry of the tissue sample and, generally, this equation represents the speed of sound in the undiffused tissue sample (i.e. a tissue sample lacking the reagent, e.g. lacking the fixation solution) at a time t=0. In the experimental embodiment, for example, the acoustic velocity of a tissue sample may be calculated by first calculating the speed of sound in the reagent based on the distance between the two ultrasound transducers (that are herein also referred to as "sensors") ($d_{sensor}$) being accurately measured as with a calibrated caliper. In this example, the sensor separation was measured with a caliper and sensor separation $d_{sensor}$=22.4 mm. Next the transit time ($t_{reagent}$) required for an acoustic pulse to traverse the reagent (lacking the tissue) between the sensors may be accurately recorded with an applicable program. In the experimental example, $t_{reagent}$=16.71 μs for a bulk reagent of 10% NBF (neutral buffered formalin). The sound velocity in the reagent ($r_{reagent}$) may then be calculated as:

$$r_{reagent} = \frac{d_{sensor}}{t_{reagent}} = \frac{22.4 \text{ mm}}{16.71 \text{ μs}} \approx 1.34 \text{ mm/μs}$$

In this experiment, a sample piece of tonsil was cored with a 6 mm histological biopsy core punch to ensure accurate and standardized sample thickness ($d_{tissue}$=6 mm), and the TOF differential (Δt) was calculated between the acoustic sensors with the tissue present ($t_{tissue+reagent}$) and without the tissue present ($t_{reagent}$):

$$\Delta t = t_{tissue+reagent} - t_{reagent}$$

$$\Delta t = 16921.3 - 16709.7 = 211.6 \text{ ns}$$

The time $t_{reagent}$ is the time required by an ultrasound signal for traversing the distance from the transmitting transducer to the receiving transducer, whereby the signal passes a reagent volume but not the tissue sample. Said traversal time can be measured e.g. by placing a biopsy capsule between the two sensors that has the same diameter as the tissue, e.g. 6 mm, and performing a TOF measurement for a signal that passes solely the reagent, not the tissue.

The time $t_{tissue}$ is the time required by an ultrasound signal for traversing the distance from the transmitting transducer to the receiving transducer, whereby the signal passes the tissue sample that does not comprise and is not surrounded by the reagent. Said traversal time can be measured e.g. by placing a biopsy capsule between the two sensors before adding the reagent to the capsule and performing a TOF measurement for a signal that passes solely the tissue.

The time differential (or "TOF differential") Δt caused by the tissue in addition to the tissue's thickness and the speed of sound in the reagent may be used to calculate the sound velocity of the undiffused tissue ($t_{tissue}$(t=0)) with the following equation derived from the known geometry (e.g. cylinder-shape, cube-shaped, box-shaped, etc.) of the sample:

$$\frac{1}{r_{tissue}(t=0)} = \frac{1}{1.34 \text{ mm/μs}} + \frac{0.2116 \text{ μs}}{6 \text{ mm}} \Rightarrow r_{tissue}(t=0) = 1.28 \text{ mm/μs}$$

Subsequently, a modeling process is executed to model the TOF over a variety of candidate diffusivity constants. The candidate diffusivity constants comprise a range of constants selected (S331) from known or prior knowledge of tissue properties obtained from the literature. The candidate diffusivity constants are not precise, but are simply based on a rough estimate of what the range may be for the particular tissue or material under observation. These estimated candidate diffusivity constants are provided to the modeling process (steps S332-S335), with a minimal of an error function being determined (S337) to obtain the true diffusivity constant of the tissue. In other words, method tracks differences between the experimentally measured TOF diffusion curve and a series of modeled diffusion curves with varying diffusivity constants.

For example, upon selecting one of a plurality of candidate diffusivity constants, the spatial dependence of the reagent concentration in the tissue sample is simulated (S332), based on a calculation of the reagent concentration $C_{reagent}$ as a function of time and space, using the solution to a heat equation for a cylindrical object:

$$c_{reagent}(t, D, x) = c_{max}\left(1 - 2\sum_{n=1}^{\infty} \frac{e^{-D\alpha_n^2 t/R_0^2} J_0(\alpha_n x/R_o)}{\alpha_n J_1(\alpha_n)}\right)$$

where x is the spatial coordinate in the depth direction of the tissue, $R_o$ is the radius of the sample, D is the candidate diffusivity constant, t is time, $J_o$ is a Bessel function of the first kind and $0^{th}$ order, $J_1$ is a Bessel function of the first kind and $1^{st}$ order, $\alpha_n$ is the location of the $n^{th}$ root of a $0^{th}$ order Bessel function, and $c_{max}$ is the maximum concentration of the reagent. In other words, the summation of the coefficient of each of these Bessel functions (higher-order differential equations), provides the constant as a function of space, time, and rate, i.e. the diffusivity constant. Although this equation is specific to the cylindrical tissue sample disclosed in these experimental embodiments, and the equation would change depending on the shape or boundary condition, the solution to the heat equation for any shape may provide the diffusivity constants for that shape.

This step is repeated for a plurality of time points (S333-S334) to obtain a time-varying TOF (that corresponds to an expected reagent concentration because the integral of the expected reagent concentration at a particular time point can be used for computing the speed of sound differential) (S335). For example, a determination is made as to whether or not the diffusion time is complete. This diffusion time may be based on the hardware or the type of system being used. For each time interval T, steps S333, S334, and S332 are repeated until the modeling time is complete upon which the modeled reagent concentration is converted to a time-varying TOF signal (S335).

In the experimental embodiment, each of the used candidate diffusion constants $D_{candidate}$ is contained in the following value range:

$$0.01 \leq D_{candidate} \leq 2 \text{ μm}^2/\text{ms}$$

Figure 5A:
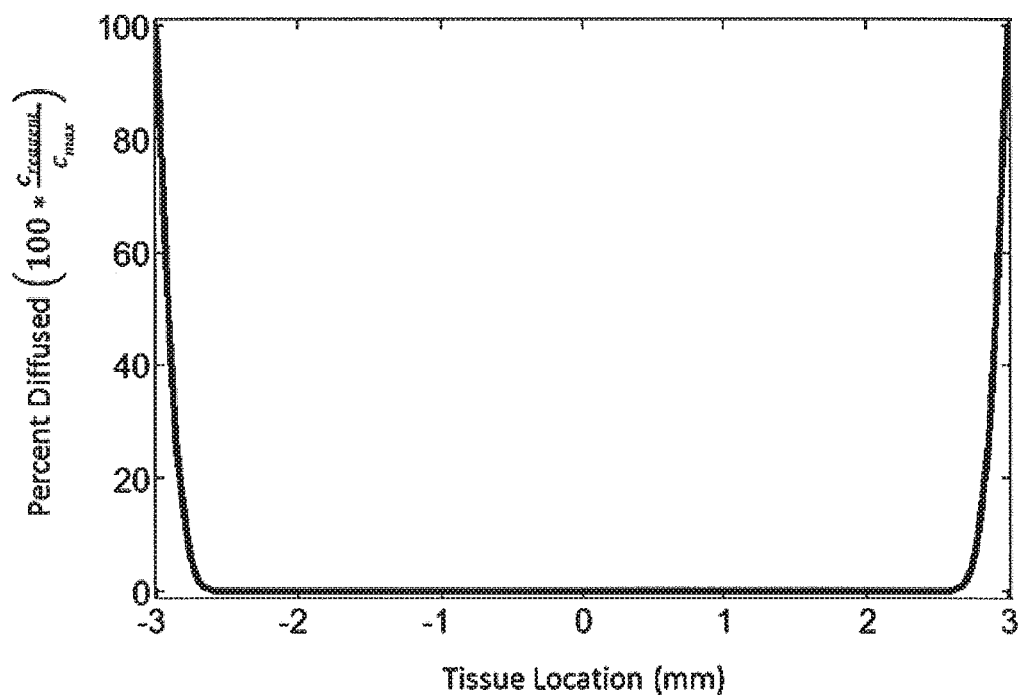
FIGS. 5A-5B respectively show a simulated concentration gradient for a first time point, and for several time points over the course of an experiment, according to an exemplary embodiment of the subject disclosure.

The tissue sample was cored with a cylindrical biopsy core punch and therefore may be well approximated by a cylinder. The solution to the heat equation above was then used to calculate an expected concentration of the reagent ($c_{reagent}$) in the tissue sample and, for the first time point in the experiment, i.e. after 104 seconds of diffusion (based on the time interval between TOF acquisitions used in the system performing the disclosed experiment), the solution representing the concentration of the reagent in the depth direction of the tissue is depicted in FIG. 5A. For example, a particular system may regularly measure a new TOF value for each of a number of different spatial locations which here are also referred to as "pixels". Each "pixel" may thus have an update rate of assigning a new TOF value, e.g. every 104 seconds.

FIG. 5A shows the simulated concentration gradient of 10% NBF into a 6 mm sample of tissue after 104 seconds of passive diffusion as calculated from the heat equation in the experimental embodiment. Moreover, these steps were repeated to determine the concentration of the reagent throughout the tissue repeatedly every 104 s over the course of the experiment (8.5 hours long in the experimental embodiment), and the result depicted in FIG. 5B.

Figure 5B:
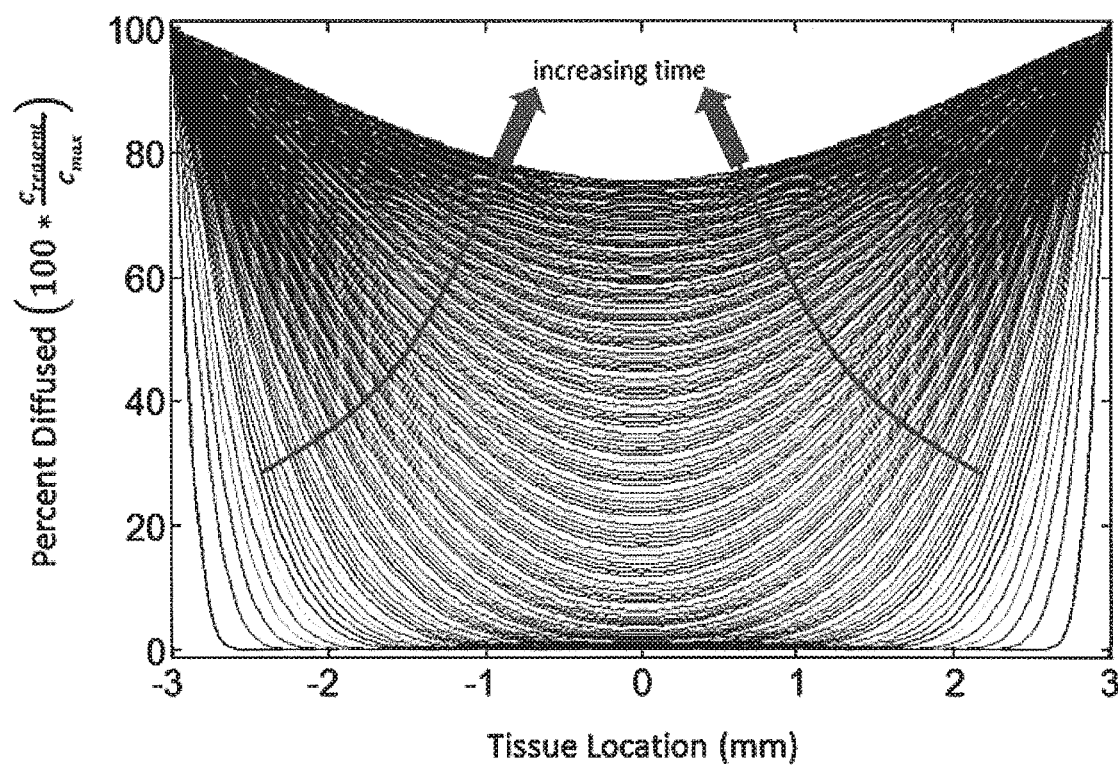

FIG. 5B shows a plot of $c_{reagent}(t, r)$ displaying the ("expected", "modeled", or "heat equation based") concentration of the reagent at all locations in the tissue (horizontal axis) as well as at all times (curves moving upward).

Referring back to FIG. 3, the results of the reagent modeling steps (S332-S334) are used to predict the contribution towards the ultrasound signal based on the fact that the ultrasound detection mechanism linearly builds up phase retardation over the depth of the tissue.

Since the ultrasound detects an integrated signal from all tissue in the depth direction, i.e. along the propagation axis of the US beam and will thus be sensitive to the integrated amount of fluid exchange in the depth direction, an "integrated expected" reagent concentration $c_{detected}$, also referred to as "detected reagent concentration", may be calculated. The "detected reagent concentration" is thus not an empirically detected value. Rather, it is a derivative value created by spatially integrating all expected reagent concentrations computed for a particular time point t and for a particular candidate diffusivity constant. The spatial integration may cover, for example, the radius of the tissue sample.

For example, the detected reagent concentration $c_{detected}$ may be calculated using:

$$c_{detected}(t) = \frac{2}{R_o} \int_0^{R_o} c_{reagent}(t, x) dx$$

According to some embodiments, the integrated reagent concentration $c_{detected}$ is used to calculate the total amount of reagent at a particular time point. For example, additional volume and/or weight information of the sample may be used for calculating absolute reagent amounts. Alternatively, the reagent amount is computed in relative units, e.g. as a percentage value indicating e.g. the volume fraction [%] of the sample being already diffused by the reagent.

After simulating (i.e., computing based on the heat equation model) the detected concentration of the reagent for a given candidate diffusivity constant and a given time point, that detected concentration may then be converted into a TOF signal (S335) as a linear combination of undiffused tissue and reagent, using:

$$TOF_{tissue}(t, D) = \frac{d_{tissue}}{r_{tissue}(t=0) + \rho c_{detecdted}(t)(r_{tissue}(t=0) - r_{reagent})}$$

where $r_{tissue}(t=0)$ is the speed of sound of undiffused tissue, and $\rho$ is the volume porosity of the tissue, representing the fractional volume of the tissue sample that is capable of fluid exchange with the bulk reagent. This equation therefore models the change in TOF signal from diffusion as a linear combination of the two distinct sound velocities (tissue and reagent). As the TOF of the respective sound velocities of pure tissue on the one hand and pure reagent on the other hand can easily be determined empirically (e.g. by respective phase-shift based TOF measurements), the amount of the reagent having already diffused into the sample at the particular time point can easily be determined.

According to embodiments, the TOF contribution of the pure tissue sample (being free of the TOF contribution of a bulk fluid such as sample buffers or the tissue fluid) can be obtained by subtracting the TOF contribution measured for the tissue sample including and/or being surrounded by the bulk fluid from the TOF contribution measured for an ultrasound signal having traversed a corresponding inter-transducer distance filled with said bulk fluid only.

Figure 6A:
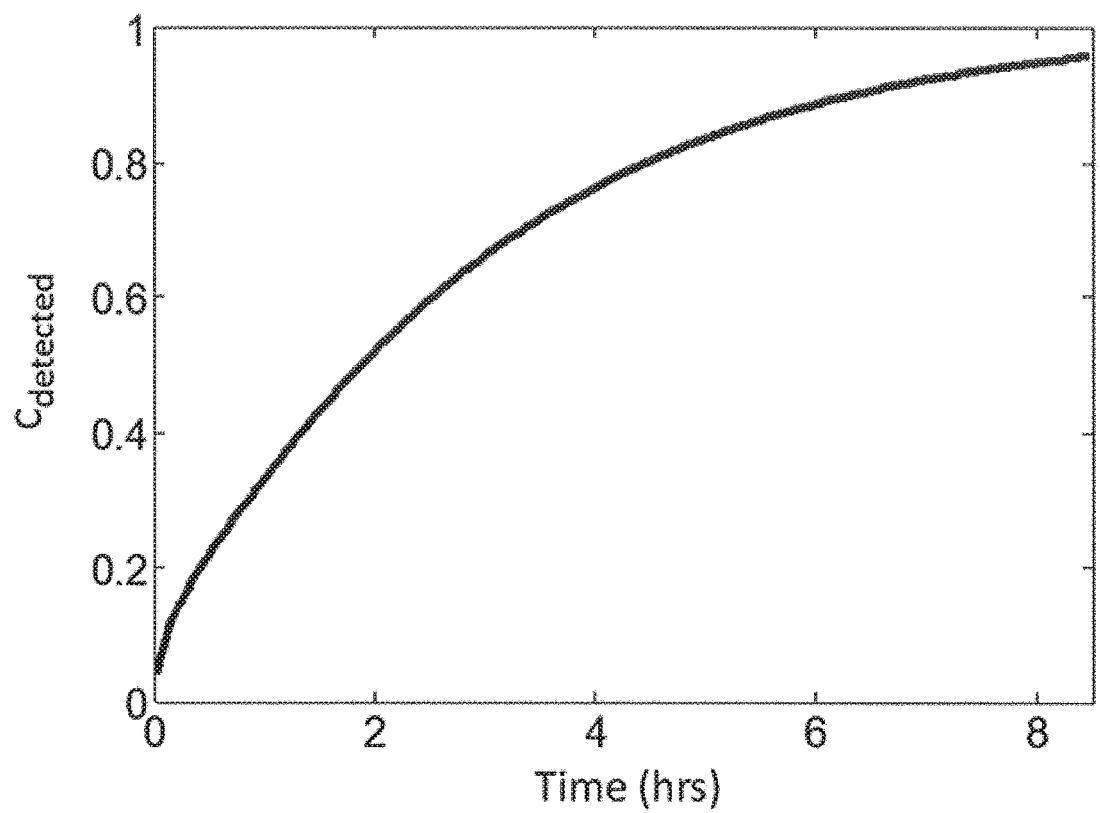
FIGS. 6A and 6B respectively depict plots of the simulated amount of detected concentration of NBF by the ultrasound over the course of the experiment and the simulated TOF signal for the first candidate diffusivity constant, according to exemplary embodiments of the subject disclosure.
Figure 6B:
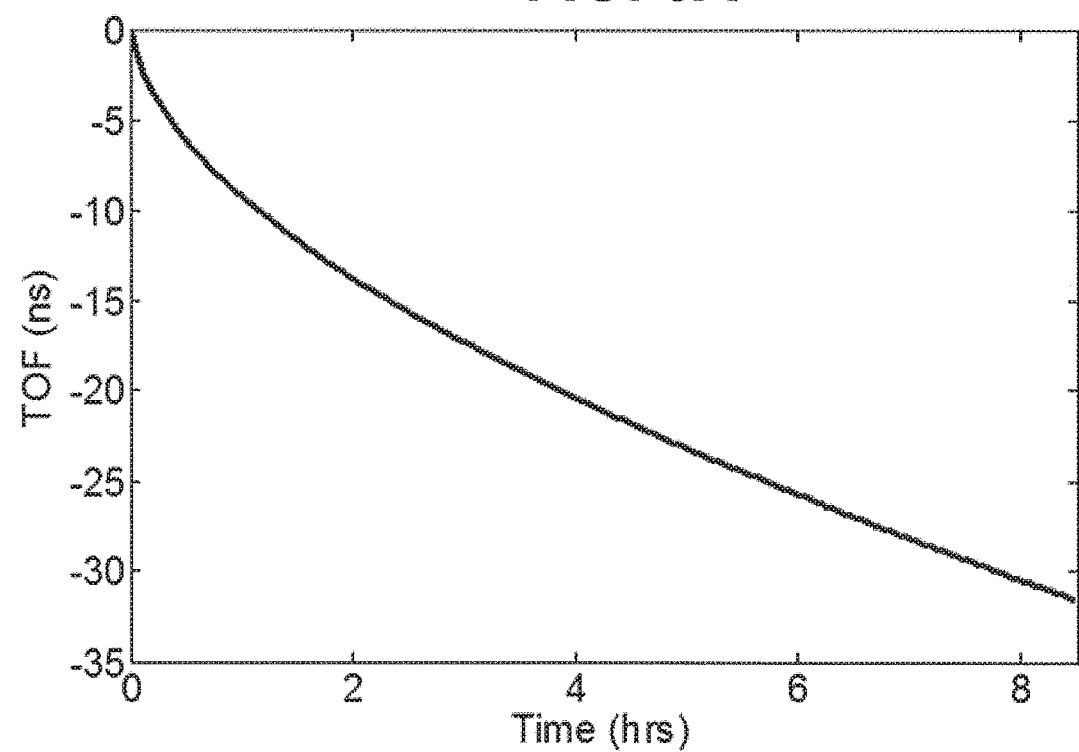

FIGS. 6A and 6B respectively depict a plot of the simulated, "detected" or "integrated" concentration of NBF by the ultrasound over the course of the experiment (FIG. 6A), and a plot of the simulated (or "expected") TOF signal for the first candidate diffusivity constant (FIG. 6B, where D=0.01 μm2/ms). The TOF signals in FIG. 6B are computed as derivatives of the respective integrated concentration of the reagent.

At this point, the method generally correlates (S336) the modeled (or "simulated" or "expected") TOF with an experimental TOF determined by measuring different spatial regions of interest (ROIs), also referred to as "candidate diffusivity points", within the tissue sample and determining a minimum of an error function to obtain a true diffusivity constant. In this example, each modeled TOF for the specific diffusion constant selected in the range specified by (S322) is correlated with the experimental TOF (S336), and determination is made as to whether or not an error is minimized (S337). If the error is not minimized, the next diffusion constant is selected (S338) and the modeling process (S332-S335) is repeated for the new diffusion constant. If it is determined that the error is minimized (S337) based on correlation (S336), then the true diffusivity constant is determined (S339) and the method ends.

Figure 4:
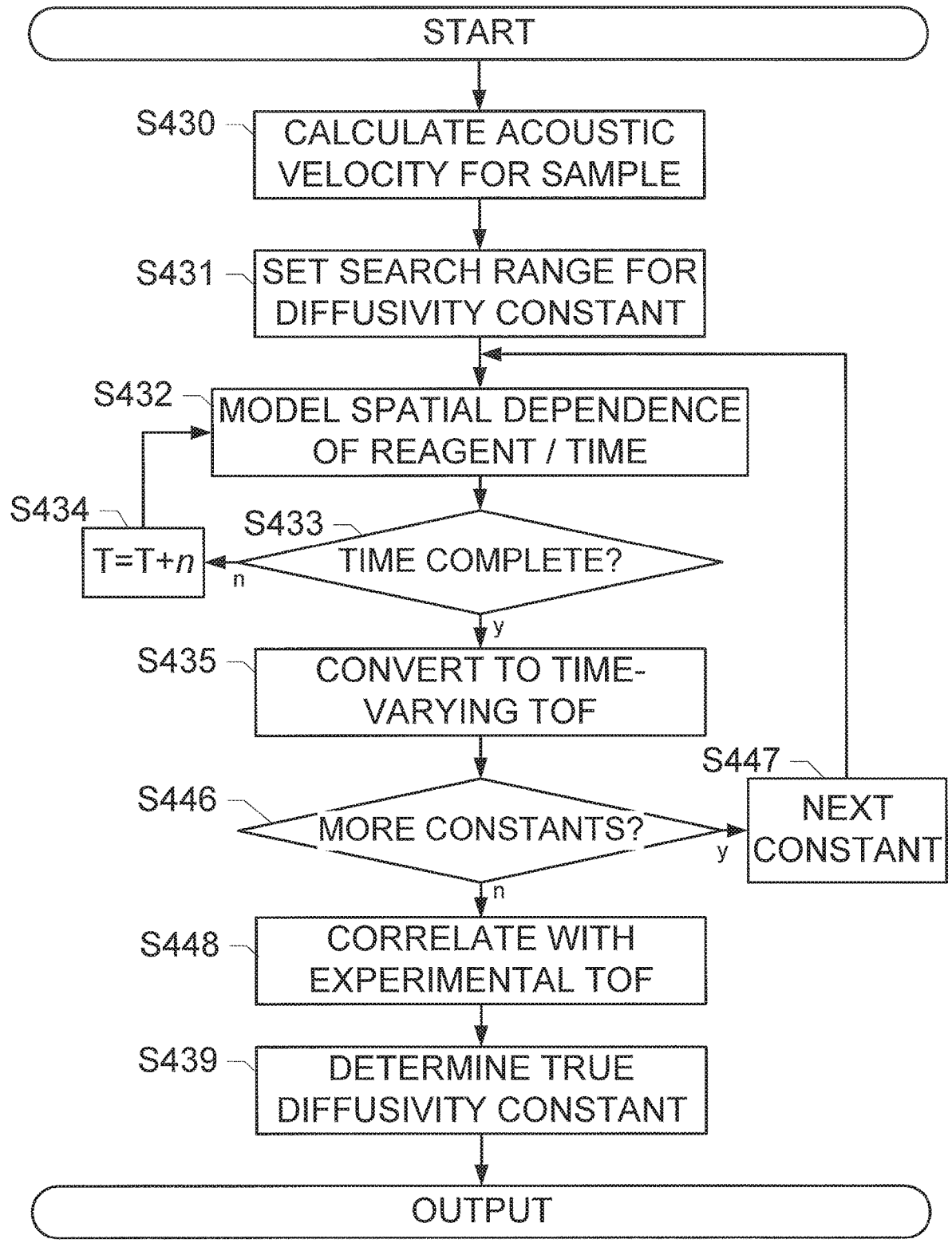
FIG. 4 shows an alternate method for obtaining a diffusivity coefficient for a tissue sample, according to an exemplary embodiment of the subject disclosure.
Figure 7:
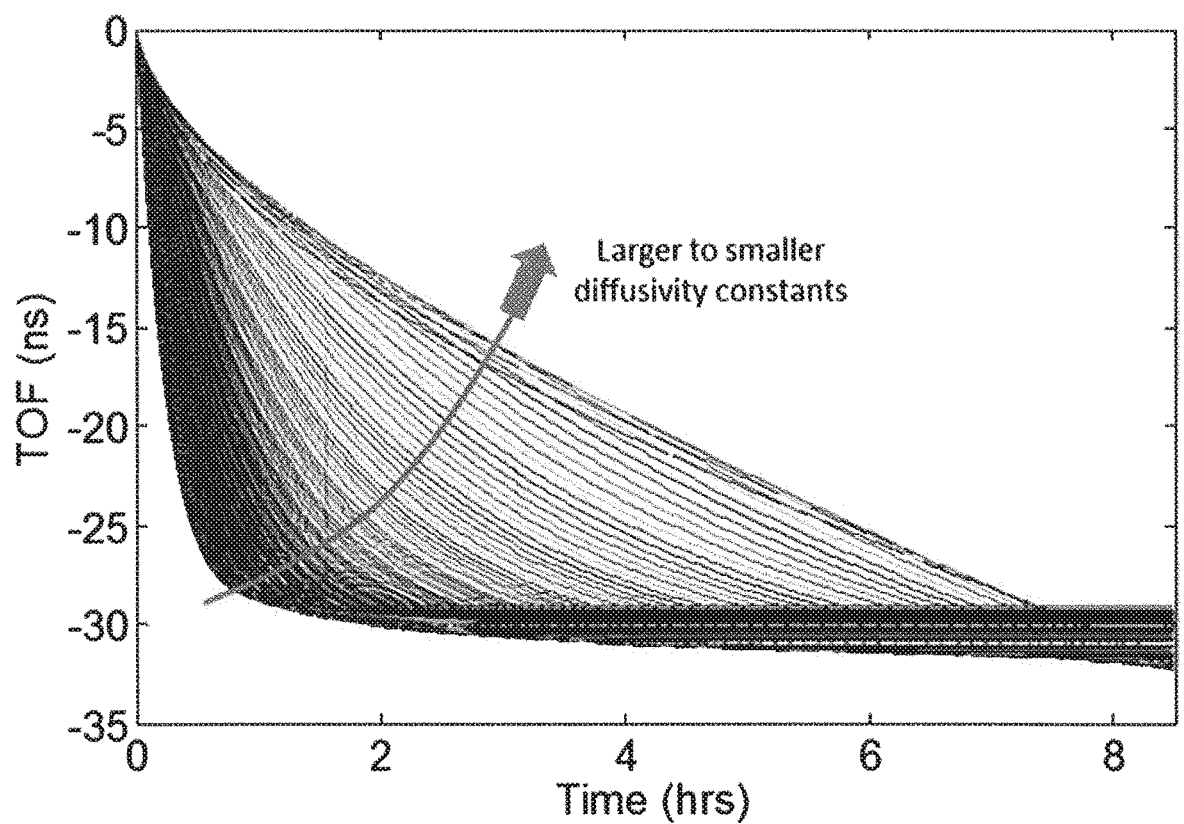
FIG. 7 depicts temporally varying TOF signals calculated for all potential diffusivity constants, according to an exemplary embodiment of the subject disclosure.

FIG. 4 shows an alternative method whereby all candidate diffusivity constants are first used to perform the modeling, based on steps S446-S447 and the correlation (S448) is performed after all the diffusivity constants are processed. A depiction of the temporally varying TOF signal calculated for all potential diffusivity constants is shown in FIG. 7. For example, FIG. 7 depicts simulated TOF traces over the 8.5 hour experiments for 6 mm tissue samples with diffusivity constants ranging from 0.01 to 2.0 μm2/ms. In the embodiment of FIG. 4, the error minimization is performed within true diffusivity constant determination step S439.

In either case, the experimental TOF must be determined for the correlation to take place. The experimental TOF may be determined by measuring different spatial regions of interest (ROIs) within the tissue. Each signal has the contribution from background reagent subtracted out to isolate the contribution from active diffusion into the tissue. Individual TOF trends are temporally smoothed via filtering. These spatially distinct TOF trends are then spatially-averaged to determine the average rate of 10% NBF diffusion into the tissue.

Figure 8B:
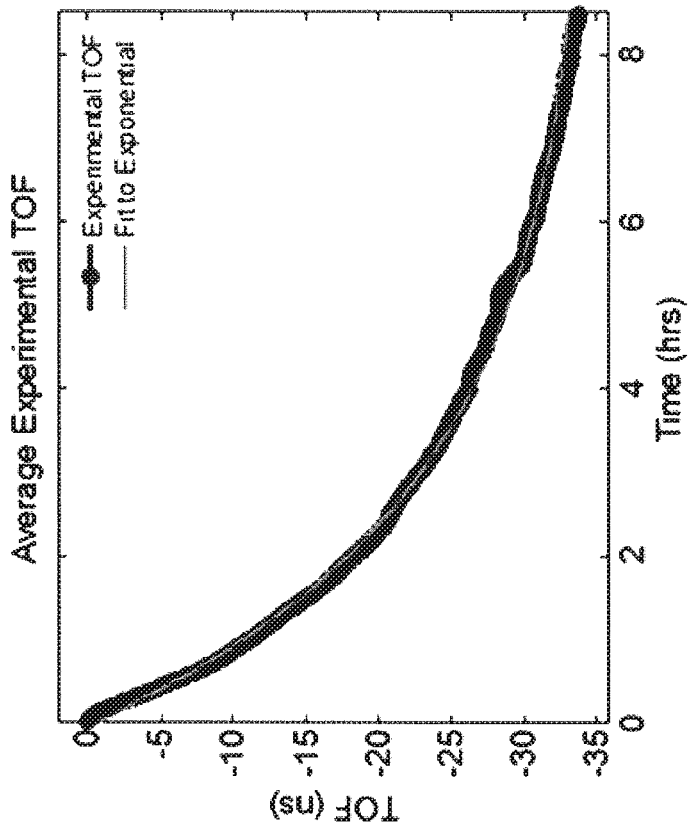
FIGS. 8A and 8B respectively depict experimentally calculated TOF trends and a spatially-averaged TOF signal collected from a 6 mm piece of human tonsil sample, according to an exemplary embodiment of the subject disclosure.
Figure 8A:
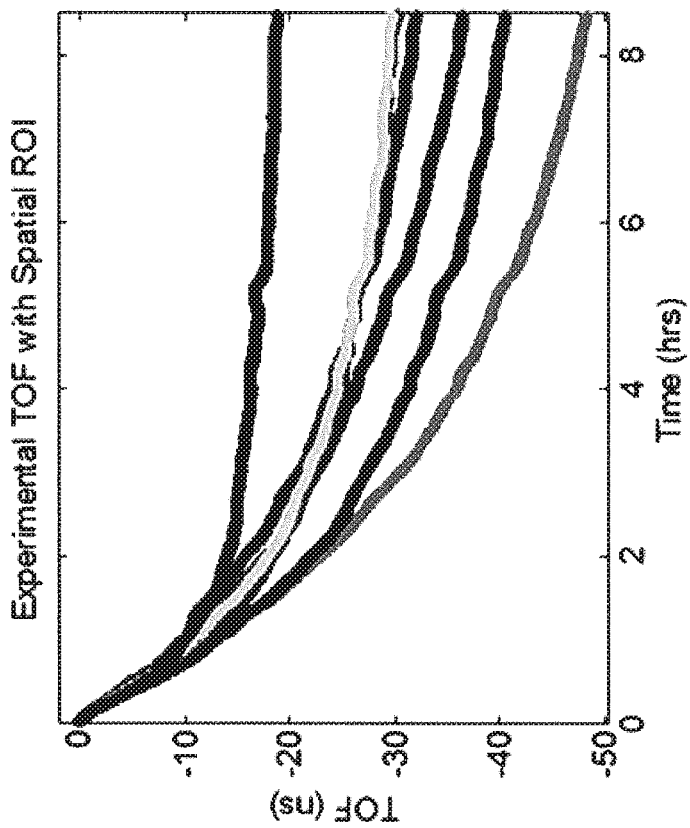

FIGS. 8A and 8B respectively depict experimentally calculated TOF trends collected from a 6 mm piece of human tonsil sample (FIG. 8A) and spatially-averaged TOF signals (FIG. 8B) representing the average rate and amount of fluid exchange of 10% NBF into the tissue.

The average rate of diffusion into the tissue is highly correlated to a single exponential signal (depicted by the dashed line in FIG. 8B), and derived by:

$$TOF_{experimental}(t) = Ae^{-t/\tau_{experimental}} + \text{offset}$$

where A is the amplitude of the TOF in nanoseconds (i.e., the TOF difference between the undiffused and fully diffused tissue sample), $\tau_{experimental}$ is the sample's decay constant representing the time required for the TOF to decay to 37% of its amplitude or equivalently to be 63% decayed and offset is a vertical offset of the above given decay function.

The 63% can be derived by the following calculation: at time $t=\tau$, $TOF(\tau)=Ae^{(-tau/tau)}=Ae^{-1}=A/e=A/2.72=0.37*A$.

It is hereby assumed that the TOF decreases with an increase in reagent concentration in the sample, but the method would likewise be applicable for reagents which increase the measured TOF upon diffusing into the sample. In the 6 mm piece of human tonsil of the experimental embodiment, $\tau_{expenmental}=2.83$ hours. Thus, from a plurality of TOFs having been experimentally determined for a plurality of consecutive time points, a decay constant of the tissue sample can be computed, e.g. by plotting the amplitudes of the TOF signal over time, analyzing the plot for identifying the offset and resolving the above solution for the decay constant.

The error correlation (S336 in FIG. 3, S448 in FIG. 4) is performed to determine an error of the modeled ("expected") TOF vs. the experimental TOF. Having calculated simulated and experimental TOF signals, a difference between the two signals may be calculated to see whether or not the candidate diffusivity constant minimizes the difference between the two signals (S337).

The error function may be computed in a couple of different ways, for instance, using one of the following:

$$\text{Error}(D) = \frac{1}{N}\sum_{t=1}^{N}(TOF_{simulated}(t, D) - TOF_{experimental}(t))^2$$

$$\text{Error}(D) = (\tau_{simulated}(D) - \tau_{experimental})^2$$

The first error function calculates the point-by-point difference between simulated ("modeled", "expected") and experimentally measured TOF signals.

The second error function exclusively compares the rate of diffusion between the simulated and modeled TOF signal by calculated the sum-squared differences between each's decay constant. The experimental decay constant $T_{experimental}$ can be obtained experimentally as described above. The "modeled", "expected" or "simulated" decay constant $T_{simulated}$ can be derived analogously from the modeled ("expected") TOFs signal of consecutive time points which also follow a decay function.

Based on the output of the error function, a true diffusivity constant may be determined (S339). The true diffusivity constant is calculated as the minimum of the error function, for instance:

$$D_{reconstructed}=\arg\min(\text{error}(D))$$

This equation enables a determination of the candidate diffusivity coefficient that produce a TOF signal as close as possible to the experimental data.

For example, with respect to the method depicted in FIG. 3, the error function may be determined for each candidate diffusivity constant until the error is minimized (S337). Alternatively, in the method of FIG. 4, the correlation with experimental TOF may be performed after all candidate diffusivity constants are processed, upon which the determination (S439) of the true diffusivity constant includes determining a minimum of the error function. The minimum of the error function is ideally zero, or as closed as possible to zero. Any error function known in the art may be used by those having ordinary skill in the art, with the goal being to minimize the error between the modeled versus experimental coefficients disclosed herein.

Figure 9A:
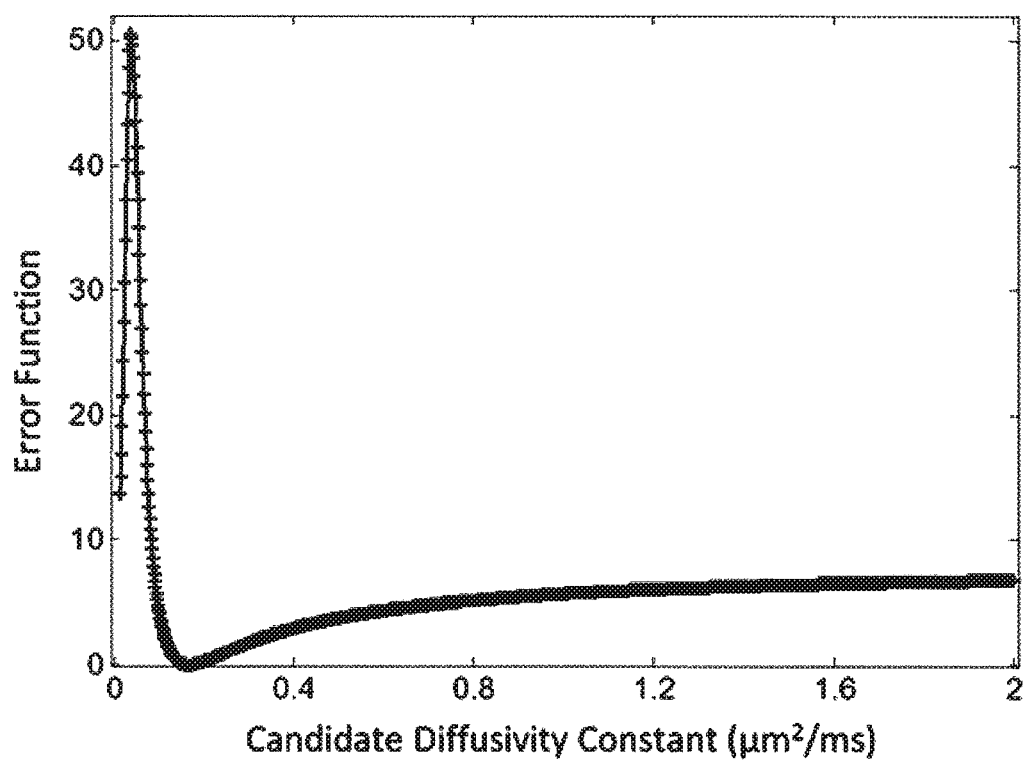
FIGS. 9A and 9B respectively show plots of the calculated error function between simulated and experimentally measured TOF signals as a function of candidate diffusivity constant and a zoomed-in view of the error function.
Figure 9B:
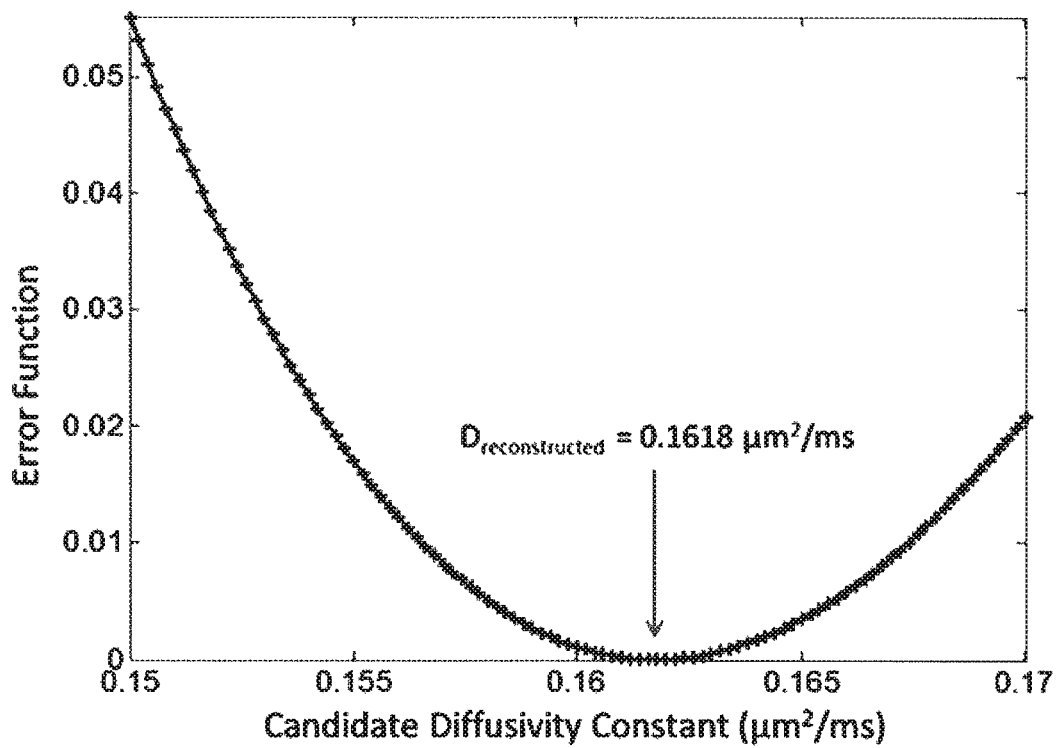
Figure 10:
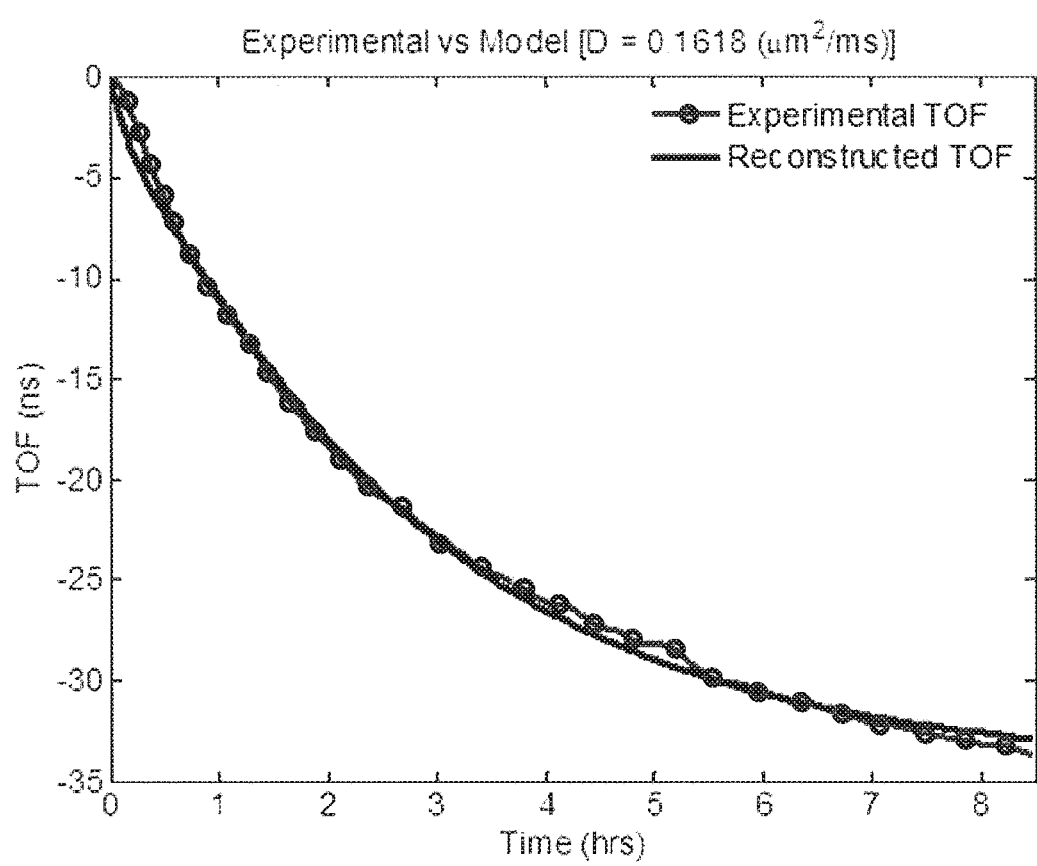
FIG. 10 depicts a TOF trend calculated with a modeled diffusivity constant plotted alongside an experimental TOF, according to an exemplary embodiment of the subject disclosure.

FIGS. 9A and 9B respectively show a plot of the calculated error function between simulated and experimentally measured TOF signals as a function of candidate diffusivity constant (FIG. 9A, $\Delta D \approx 10^{e-5}$ µm$^2$/ms.), and a zoomed-in view of the error function (FIG. 9B). In the experimental embodiment, the minimum of the error function was calculated to be at D=0.1618 µm$^2$/ms. The validity of the reconstructed constant was tested and used to back-simulate a TOF trend. FIG. 10 depicts the TOF trend calculated with this diffusivity constant and plotted alongside the experimental TOF measured with the 6 mm piece of human tonsil. In FIG. 10, the plot shows the experimentally calculated TOF trend from a 6 mm piece of human tonsil in 10% NBF (dotted line) and the modeled TOF trend for $D_{reconstructed}=0.168$ µm$^2$/ms (solid line). In this embodiment, $\tau_{experimental2}=2.830$ hrs and $\tau_{simulated}=2.829$ hrs.

Figure 11B:
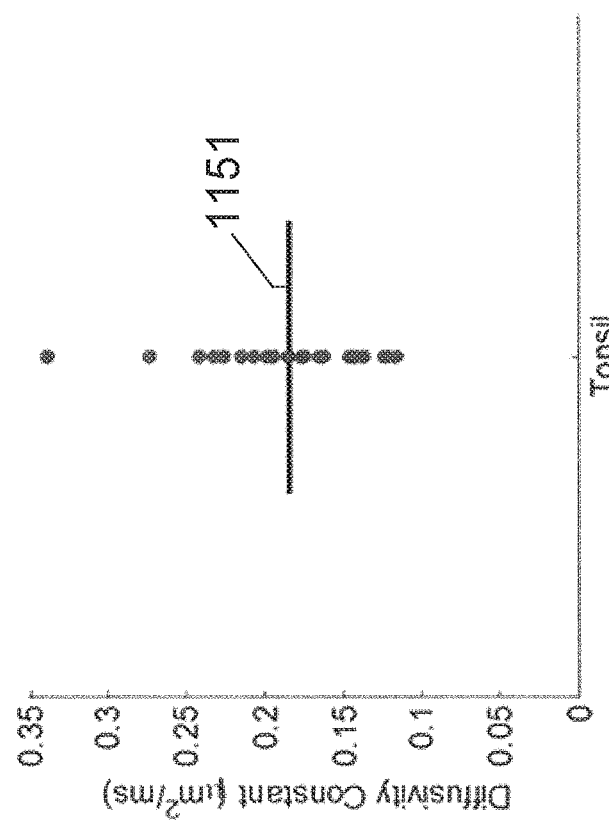
FIGS. 11A and 11B.
Figure 11A:
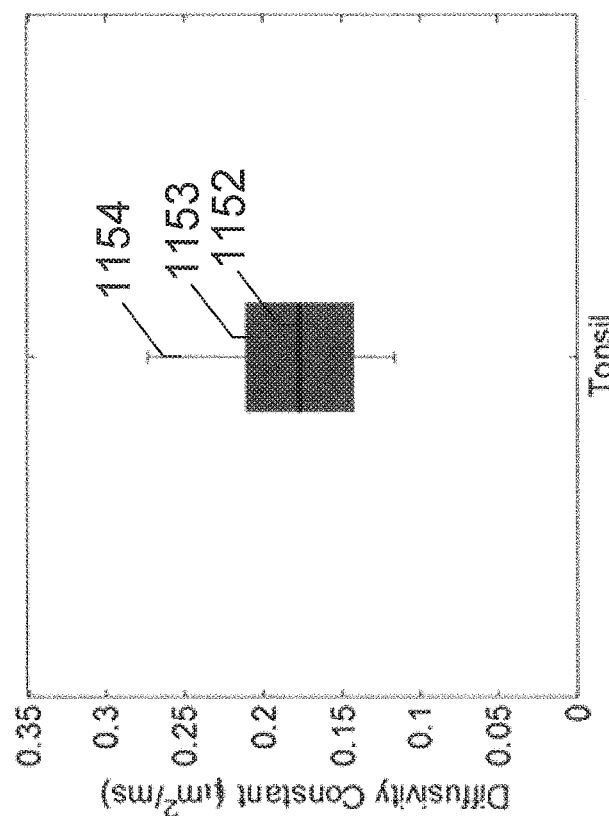

Furthermore, this same procedure was repeated for several specimens of 6 mm human tonsil samples, with successfully reconstructed diffusivity constants for all samples, as depicted in FIGS. 11A and 11B. FIG. 11A shows reconstructed diffusivity constants for the 23 samples of 6 mm human tonsil. Line 1151 represents the average. FIG. 11B shows a box and whisker plot displaying the distribution of the reconstructed diffusivity constants. Line 1152 represents the median value, and the box 1153 extends from the 25-75 percentiles, with whiskers 1154 extending from the 5-95 percentiles. Overall, the algorithm predicted 6 mm tonsils samples have an average diffusivity constant of 0.1849 µm2/ms with a relative tight distributed producing a standard deviation of 0.0545 µm2/ms.

Figure 12A:
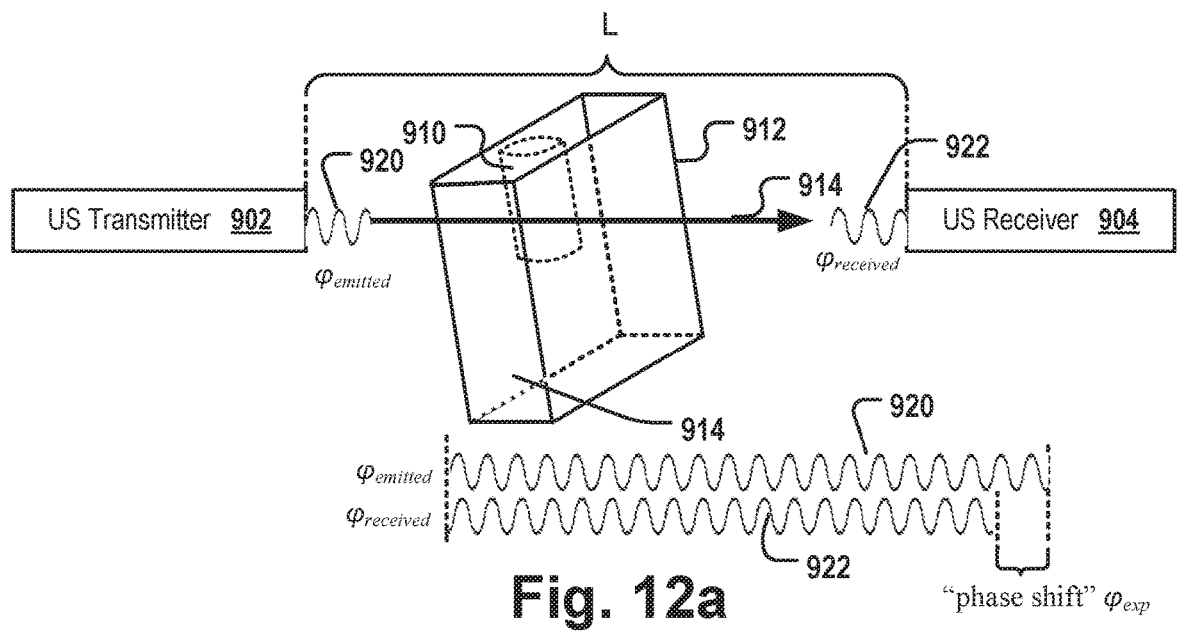
FIGS. 12A-12B show a system comprising a transmitter and a receiver pair for measuring TOF via phase shifts.

FIG. 12A shows a system for monitoring the time-of-flight of an ultrasound signal according to embodiments of the invention. An ultrasound-based time-of-flight (TOF) monitoring system may comprise one or more pairs of transducers (e.g. TA0040104-10, CNIRHurricane Tech) for performing the time-of-flight measurements based on a phase shift of the ultrasound signals. In the embodiment depicted in FIG. 12A, the system comprises at least one pair of transducers consisting of an ultrasound ("US") transmitter 902 and an ultrasound receiver 904 which are spatially aligned to each other such that a tissue sample 910 which is placed in the beam path 914 from the transmitter to the receiver is located at our close to the common foci of said two transducers 902, 904. The tissue sample 910 can be contained, for example, in a sample container 912 (e.g. a standard histological cassette like "CellSafe 5" of CellPath or a biopsy capsule like "CellSafe Biopsy Capsules" of CellPath) that is filled with a fixation solution. Phase-shift based TOF measurements are performed before and after the biopsy capsule 912 is filled with the fixation solution and while the solution slowly diffuses into the sample. The one transducer acting as the transmitter sends out an acoustic pulse that traverses the tissue and is detected by the other transducer acting as the receiver. The total distance between two transducers constituting a transmitter-receiver transducer pair is referred to as "L". The total time the ultrasound signal needs to traverse the distance between the transmitter 902 and the receiver 904 may be referred to as time-of-flight of said signal. The transmitter 902 may be focused, for example, at 4 MHz and support a frequency sweep range of 3.7-4.3 MHz.

According to embodiments, the distance L is assumed here to be known, at least approximately. For example, the distance of the transducers may be accurately measured (e.g. by optic, ultrasound based or other measurement techniques) or may be disclosed by a manufacturer of the acoustic monitoring system.

The transmitting transducer 902 is programmable with a waveform generator (e.g. AD5930 from Analog Devices) to transmit a sinusoidal wave (or "sinusoidal signal") for a defined frequency for a defined time interval, e.g. several hundred microseconds. That signal is detected by the receiving transducer 904 after traversing the fluid and/or tissue. The received ultrasound signal 922 and the emitted (also referred to as "transmitted") sinusoid signal 920 are compared electronically with a digital phase comparator (e.g. AD8302, Analog Devices).

A "received" "signal" (or wave) as used herein is a signal whose properties (phase, amplitude, and/or frequency, etc.) are identified and provided by a transducer, e.g. receiver 904, that receives said signal. Thus, the signal properties are identified after said signal has passed a sample or any other kind of material.

A "transmitted" or "emitted" "signal" (or wave) as used herein is a signal whose properties (phase, amplitude, and/or frequency, etc.) are identified by a transducer, e.g. transmitter 902 that emits the signal. Thus, the signal properties are identified before the signal has passed a sample or any other kind of material.

For example, the transmitted signal may be characterized by signal properties identified by the transmitting transducer, the received signal may be characterized by signal properties measured by the receiving transducer, whereby the transmitting and the receiving transducer are operatively coupled to a phase comparator of the acoustic monitoring system.

Figure 12B:
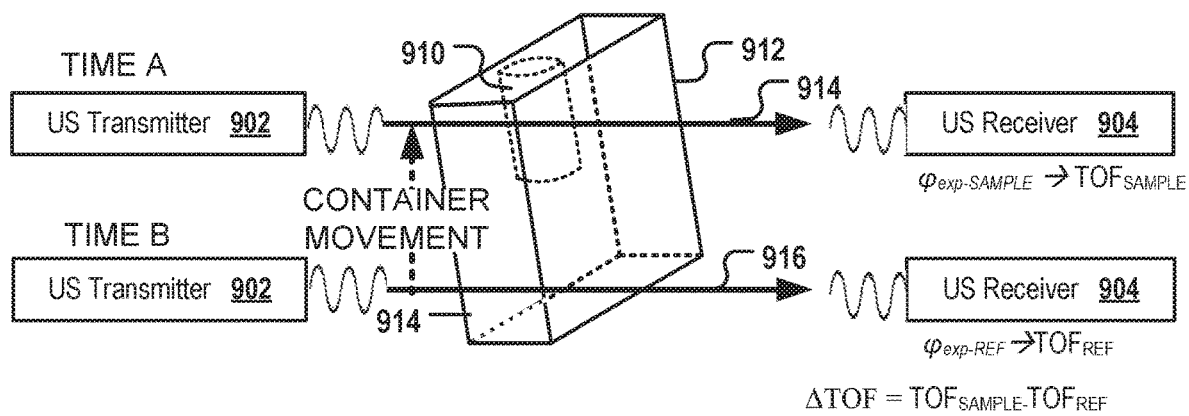

FIG. 12B depicts the determination of the TOF for the pure reagent from which the speed of the sound wave for the beam path crossing the pure reagent without the sample can be inferred. In this embodiment, the one or more transducer pairs 902, 904 and the sample container 912 can be moved relative to each other. Preferentially, the system comprises a container holder capable of repositioning the container 912 such that the US beam traverses a region 914 of the container that solely comprises the fixation solution but not the tissue.

At a time A, when the tissue is not yet immersed in a fixation solution, the TOF for a sound signal traversing the distance between the transducers is obtained via a measured phase shift $\varphi_{exp}$ as described for FIG. 12A. In this case, the beam path crosses a sample being free of the reagent. As L is known, the measured TOF can be used for computing the speed of the sound signal for traversing the distance in the presence of the undiffused sample.

At a time B, when the tissue is immersed in a fixation solution, the TOF for a sound signal traversing the distance between the transducers is obtained via a measured phase shift $\varphi_{exp}$. In this case, the beam path crosses a sample container comprising only the reagent, not the sample (or crosses the sample container at a position that is free of the sample). As L is known, the measured TOF can be used for computing the speed of the sound signal for traversing the distance in the presence of the reagent (and the sample container) only, i.e., in the absence of the sample in the beam path. Time A and time B may represent identical time points in case a further transducer pair is configured for performing the two measurements in parallel.

In a further aspect, the invention relates to a system 100 comprising an acoustic monitoring device that detects acoustic waves 922 having traveled through a porous material 910 and a computing device 101 communicatively coupled to the acoustic monitoring device 102. The computing device includes instructions which, when executed, cause the computing device to perform operations comprising:

computing a set of experimental TOFs from measured acoustic data of the detected acoustic waves, each experimental TOF indicating the TOF of acoustic waves that have traveled through a candidate diffusivity point of the porous material at a respective one of a plurality of time points; the candidate diffusivity point is a location in or at the surface of the porous material;

setting a range of candidate diffusivity constants for the porous material;

for each of the candidate diffusivity constants, simulating a spatial dependence concentration model of an expected concentration of a reagent within the porous material for the plurality of time points and for the candidate diffusivity point, the expected concentration of the reagent being a function of time, space and said candidate diffusivity constant;

using the spatial dependence concentration model for computing a spatial dependence TOF model for the porous material, the TOF model assigning, to the candidate diffusivity point, for each of the plurality of time points and for each of the candidate diffusivity constants, a respectively modeled TOF; the expressions "modeled", "simulated" and "expected" are used herein interchangeably; for example, the "use" may consist of converting the spatial dependence concentration model to the spatial dependence TOF model; and determining an error function for the candidate diffusivity point, the error being indicative of a distance (that may also be considered as and referred to as an "error") between each of the modeled TOFs assigned to said candidate diffusivity point from a corresponding experimental TOF, the experimental TOF having been measured by the acoustic monitoring device at the same time point as used for modeling its corresponding modeled TOF;

using the error function for identifying one or more modeled TOFs having minimum distances to the corresponding experimental TOFs;

outputting a diffusivity constant calculated for the porous material from the candidate diffusivity constants of the one or more identified modeled TOFs.

In a further aspect, the invention relates to a corresponding method.

According to embodiments, the computing the spatial dependence TOF model comprises determining each of the modeled TOFs by solving a heat equation for the porous material.

According to embodiments, the computing of a set of experimental TOFs is performed for two or more candidate diffusivity points of the porous material. The spatial dependence concentration model is a computer model, e.g. a set of one or more modeling functions, that indicates an expected concentration of a reagent within the porous material for the plurality of time points and for each of the two or more candidate diffusivity points. The spatial dependence TOF model assigns, to each of the two or more candidate diffusivity point, for each of the plurality of time points and for each of the candidate diffusivity constants, a respectively modeled (or "expected") TOF.

According to embodiments, the acoustic data comprises: the velocity of the sound waves in the porous material prior to diffusion with the reagent; and/or the experimental TOFs of the acoustic waves through the porous material at the plurality of time points during diffusion of the reagent into the porous material; and/or experimental phase shift data for computing the experimental TOFs from the experimental phase shift data; and/or velocity of the sound waves in the reagent being free of the porous material; and/or a thickness of the porous material. For example, said thickness is determined, according to embodiments, using a pulse echo ultrasound.

According to embodiments, the computation of the spatial dependence TOF model comprises:

selecting a first one of the candidate diffusivity constants;
calculating an expected reagent concentration $c_{reagent}$ at each of the plurality of candidate diffusivity points in the porous material for each of the plurality of time points in dependence of the selected candidate diffusivity constant;
calculating an integrated reagent concentration $c_{detected}$ for each of the plurality of time points and for each of the candidate diffusivity constants by integrating the expected reagent concentration $c_{reagent}$ calculated for said time point and said candidate diffusivity constant over a radius of the porous material;
converting the integrated reagent concentration to a modeled TOF of the spatial dependence TOF model by computing a linear combination of the speed of the sound waves in the porous material prior to diffusion with the reagent and the speed of the sound waves in the reagent being free of the porous material; and
selecting a next one of the candidate diffusivity constants and repeating this step and the three previous steps for the next selected candidate diffusivity constant until a termination criterion is reached.

In summary, determination of diffusivity constants for any sample material may be provided by calculating the speed of sound in a reagent at a given temperature, pressure, etc., determining the sample's thickness with standard pulse echo ultrasound, determining the absolute sound velocity in the undiffused sample via phase retardation of ultrasound, followed by generating the modeled TOF trend from the candidate diffusivity constant first simulating the spatial dependence of the reagent diffusion into the sample, summing the total reagent concentration detected by the ultrasound beam, converting the detected reagent concentration to the TOF differential, and repeating these steps for multiple diffusion times. Then, the modeled TOF trend is determined by repeating the spatial dependence simulation for a plurality of candidate diffusivity constants (as provided by the known literature) and calculating an error between the experimental and simulated TOF differentials at all times and for all diffusivity constants, resulting in an error function between the experimental and modeled TOF as a function of diffusivity constant. Calculating the true diffusivity constant as the minimum of the error function results in an output.

Moreover, the subject disclosure applies to both biological and non-biological context, providing an ability to reconstruct the diffusivity constant of any substance based on the acoustic TOF curve. The disclosed methods are more sensitive and accurate when compared to prior art methods. Although the disclosed operations provide fitting the TOF curve to a single exponential function comprising a summation of Bessel functions, a double exponential or quadratic function may be more appropriate, depending on the context. Therefore, the equation itself may change, while the novel features disclosed herein may maintain their inventive spirit and scope when read by a person having ordinary skill in the art.

III. Exemplary Applications of the Present Systems and Methods

Diffusivity constant calculations are known to be useful for many applications, including compositional analysis. The present systems and methods are contemplated to be used in any system that utilizes a diffusivity constant measurement. In one specific embodiment, the present systems and methods are applied to the field of monitoring diffusion of fluids into porous materials.

In one particular embodiment, the porous material is a tissue sample. In many common tissue analysis methods, the tissue sample is diffused with a fluid solution. For example, Hine (Stain Technol. 1981 March; 56(2):119-23) discloses a method of staining whole tissue blocks by immersing a tissue sample in a hematoxylin solution and eosin solution after fixation and prior to embedding and sectioning. Additionally, fixation is frequently performed by immersing an unfixed tissue sample into a volume of fixative solution, and the fixative solution is allowed to diffuse into the tissue sample. As demonstrated by Chafin et al., (PLoS ONE 8(1): e54138. doi:10.1371/journal.pone. 0054138 (2013)), a failure to ensure that a fixative has sufficiently diffused into the tissue can compromise the integrity of the tissue sample. Thus, in one embodiment, the present systems and methods are applied to determine a sufficient time of diffusion of a fixative into a tissue sample. In such a method, the user selects a minimum fixative concentration to be achieved at a particular point in the tissue sample (such as the center of the thickness of the tissue sample). Knowing at least the tissue thickness, tissue geometry, and the calculated true diffusivity constant, a person of ordinary skill in the art could apply well-known "diffusion" or "diffusivity" algorithms to determine a minimum time to reach the minimum fixative concentration at the center of the tissue sample. The fixative will thus be allowed to diffuse into the tissue sample for at least said minimum time.

In an embodiment, the present systems and methods are used to run a two-temperature immersion fixation method on a tissue sample. As used herein, a "two-temperature fixation method" is a fixation method in which tissue is first immersed in cold fixative solution for a first period of time, followed by heating the tissue for the second period of time. The cold step permits the fixative solution to diffuse throughout the tissue without substantially causing cross-linking. Then, once the tissue has adequately diffused throughout the tissue, the heating step leads to cross-linking by the fixative. The combination of a cold diffusion followed by a heating step leads to a tissue sample that is more completely fixed than by using standard methods. Thus, in an embodiment, a tissue sample is fixed by: (1) immersing an unfixed tissue sample in a cold fixative solution and monitoring diffusion of the fixative into the tissue sample by monitoring TOF in the tissue sample using the systems and methods as disclosed herein (diffusion step); and (2) allowing the temperature of the tissue sample to raise after a threshold TOF has been measured (fixation step). In exemplary embodiments, the diffusion step is performed in a fixative solution that is below 20° C., below 15° C., below 12° C., below 10° C., in the range of 0° C. to 10° C., in the range of 0° C. to 12° C., in the range of 0° C. to 15° C., in the range of 2° C. to 10° C., in the range of 2° C. to 12° C., in the range of 2° C. to 15° C., in the range of 5° C. to 10° C., in the range of 5° C. to 12° C., in the range of 5° C. to 15° C. In exemplary embodiments, the environment surrounding the tissue sample is allowed to rise within the range of 20° C. to 55° C. during the fixation step. In certain embodiments, the fixative is an aldehyde-based cross-linking fixative, such as glutaraldehyde- and/or formalin-based solutions. Examples of aldehydes frequently used for immersion fixation include:

formaldehyde (standard working concentration of 5-10% formalin for most tissues, although concentrations as high as 20% formalin have been used for certain tissues);

glyoxal (standard working concentration 17 to 86 mM);

glutaraldehyde (standard working concentration of 200 mM).

Aldehydes are often used in combination with one another. Standard aldehyde combinations include 10% formalin+1% (w/v) Glutaraldehyde. Atypical aldehydes have been used in certain specialized fixation applications, including: fumaraldehyde, 12.5% hydroxyadipaldehyde (pH 7.5), 10% crotonaldehyde (pH 7.4), 5% pyruvic aldehyde (pH 5.5), 10% acetaldehyde (pH 7.5), 10% acrolein (pH 7.6), and 5% methacrolein (pH 7.6). Other specific examples of aldehyde-based fixative solutions used for immunohistochemistry are set forth in Table 1:

TABLE 1

| Solution | Standard Composition |
|---|---|
| Neutral Buffered Formalin | 5-20% formalin + phosphate buffer (pH ~6.8) |
| Formal Calcium | 10% formalin + 10 g/L calcium chloride |
| Formal Saline | 10% formalin + 9 g/L sodium chloride |
| Zinc Formalin | 10% formalin + 1 g/L zinc sulphate |
| Helly's Fixative | 50 mL 100% formalin + 1 L aqueous solution containing 25 g/L potassium dichromate + 10 g/L sodium sulfate + 50 g/L mercuric chloride |
| B-5 Fixative | 2 mL 100% formalin + 20 mL aqueous solution containing 6 g/L mercuric chloride + 12.5 g/L sodium acetate (anhydrous) |
| Hollande's Solution | 100 mL 100% formalin + 15 mL Acetic acid + 1 L aqueous solution comprising 25 g copper acetate and 40 g picric acid |
| Bouin's Solution | 250 mL 100% formalin + 750 mL saturated aqueous picric acid + 50 mL glacial acetic acid |

In certain embodiments, the fixative solution is selected from Table 1. In some embodiments, the aldehyde concentration used is higher than the above-mentioned standard concentrations. For example, a high-concentration aldehyde-based fixative solution can be used having an aldehyde concentration that is at least 1.25-times higher than the standard concentration used to fix a selected tissue for immunohistochemistry with a substantially similar composition. In some examples, the high-concentration aldehyde-based fixative solution is selected from: greater than 20% formalin, about 25% formalin or greater, about 27.5% formalin or greater, about 30% formalin or greater, from about 25% to about 50% formalin, from about 27.5% to about 50% formalin, from about 30% to about 50% formalin, from about 25% to about 40% formalin, from about 27.5% to about 40% formalin, and from about 30% to about 40% formalin. As used in this context, the term "about" shall encompass concentrations that do not result in a statistically significant difference in diffusion at 4° C. as measured by Bauer et al., *Dynamic Subnanosecond Time-of-Flight Detection for Ultra precise Diffusion Monitoring and Optimization of Biomarker Preservation*, Proceedings of SPIE, Vol. 9040, 90400B-1 (2014 Mar. 20).

Two-temperature fixation processes are especially useful for methods of detecting certain labile biomarkers in tissue samples, including, for example, phosphorylated proteins, DNA, and RNA molecules (such as miRNA and mRNA). See PCT/EP2012/052800 (incorporated herein by reference). Thus, in certain embodiments, the fixed tissue samples obtained using these methods can be analyzed for the presence of such labile markers. Thus in an embodiment, a method of detecting a labile marker is a sample is provided, said method comprising fixing the tissue according to a two-temperature fixation as disclosed herein and contacting the fixed tissue sample with an analyte binding entity capable of binding specifically to the labile marker. Examples of analyte-binding entities include: antibodies and antibody fragments (including single chain antibodies), which bind to target antigens; t-cell receptors (including single chain receptors), which bind to MHC:antigen complexes; MHC: peptide multimers (which bind to specific T-cell receptors); aptamers, which bind to specific nucleic acid or peptide targets; zinc fingers, which bind to specific nucleic acids, peptides, and other molecules; receptor complexes (including single chain receptors and chimeric receptors), which bind to receptor ligands; receptor ligands, which bind to receptor complexes; and nucleic acid probes, which hybridize to specific nucleic acids. For example, an immunohistochemical method of detecting a phosphorylated protein in a tissue sample is provided, the method comprising contacting the fixed tissue obtained according to the foregoing two-temperature fixation method with an antibody specific for the phosphorylated protein and detecting binding of the antibody to the phosphorylated protein. In other embodiments, an in situ hybridization method of detecting a nucleic acid molecule is provided, said method comprising contacting the fixed tissue obtained according to the foregoing two-temperature fixation method with a nucleic acid probe specific for the nucleic acid of interest and detecting binding of the probe to the nucleic acid of interest.

IV. Other Embodiments of the Disclosed System and Method

Embodiment 1

A system (100) comprising: an acoustic monitoring device that detects acoustic waves (922) having traveled through a porous material (910); and a computing device (101) communicatively coupled to the acoustic monitoring device (102), the computing device including instructions which, when executed, cause the computing device to perform operations comprising: computing a set of experimental TOFs from measured acoustic data of the detected acoustic waves, each experimental TOF indicating the TOF of acoustic waves that have traveled through a candidate diffusivity point of the porous material at a respective one of a plurality of time points; setting a range of candidate diffusivity constants for the porous material; for each of the candidate diffusivity constants, simulating a spatial dependence concentration model of an expected concentration of a reagent within the porous material for the plurality of time points and for the candidate diffusivity point, the expected concentration of the reagent being a function of time, space and said candidate diffusivity constant; using the spatial dependence concentration model for computing a spatial dependence TOF model for the porous material, the TOF model assigning, to the candidate diffusivity point, for each of the plurality of time points and for each of the candidate diffusivity constants, a respectively modeled TOF; and determining an error function for the candidate diffusivity point, the error being indicative of a distance between each of the modeled TOFs assigned to said candidate diffusivity point from a corresponding experimental TOF, the experimental TOF having been measured by the acoustic monitoring device at the same time point as used for modeling its corresponding modeled TOF; using the error function for identifying one or more modeled TOFs having minimum distances to the corresponding experimental TOFs; and, outputting a diffusivity constant calculated for the porous material from the candidate diffusivity constants of the one or more identified modeled TOFs.

Embodiment 2

A method for determining a diffusivity constant of a porous material (910) comprising: computing a set of experimental TOFs from measured acoustic data of acoustic waves (922), the acoustic waves having been detected by an acoustic monitoring device (102) and having traveled through the porous material (910), each experimental TOF indicating the TOF of acoustic waves that have traveled through a candidate diffusivity point of the porous material at a respective one of a plurality of time points; setting a range of candidate diffusivity constants for the porous material; for each of the candidate diffusivity constants, simulating a spatial dependence concentration model of an expected concentration of a reagent within the porous material for the plurality of time points and for the candidate diffusivity point, the expected concentration of the reagent being a function of time, space and said candidate diffusivity constant; using the spatial dependence concentration model for computing a spatial dependence TOF model for the porous material, the TOF model assigning, to the candidate diffusivity point, for each of the plurality of time points and for each of the candidate diffusivity constants, a respectively modeled TOF; and, determining an error function for the candidate diffusivity point, the error being indicative of a distance between each of the modeled TOFs assigned to said candidate diffusivity point from a corresponding experimental TOF, the experimental TOF having been measured by the acoustic monitoring device at the same time point as used for modeling its corresponding modeled TOF; using the error function for identifying one or more modeled TOFs having minimum distances to the corresponding experimental TOFs; outputting a diffusivity constant calculated for the porous material from the candidate diffusivity constants of the one or more identified modeled TOFs.

Embodiment 3

The method of embodiment 2, wherein computing the spatial dependence TOF model comprises determining each of the modeled TOFs by solving a heat equation for the porous material.

Embodiment 4

The method of any one of embodiments 2-3, the computing of a set of experimental TOFs being performed for two or more candidate diffusivity points of the porous material, the spatial dependence concentration model indicating an expected concentration of a reagent within the porous material for the plurality of time points and for each of the two or more candidate diffusivity points, the spatial dependence TOF model assigning, to each of the two or more candidate diffusivity point, for each of the plurality of time points and for each of the candidate diffusivity constants, a respectively modeled TOF.

Embodiment 5

The method of any one of embodiments 2-4, the acoustic data comprising: velocity of the sound waves in the porous material prior to diffusion with the reagent; and/or the experimental TOFs of the acoustic waves through the porous material at the plurality of time points during diffusion of the reagent into the porous material; and/or experimental phase shift data for computing the experimental TOFs from the experimental phase shift data; velocity of the sound waves in the reagent being free of the porous material; and/or a thickness of the porous material.

Embodiment 6

The method of any one of embodiments 2-5, the computation of the spatial dependence TOF model comprising: selecting a first one of the candidate diffusivity constants; calculating an expected reagent concentration ($c_{reagent}$) at each of the plurality of candidate diffusivity points in the porous material for each of the plurality of time points in dependence of the selected candidate diffusivity constant; calculating an integrated reagent concentration ($c_{detected}$) for each of the plurality of time points and for each of the candidate diffusivity constants by integrating the expected reagent concentration ($c_{reagent}$) calculated for said time point and said candidate diffusivity constant over a radius of the porous material; converting the integrated reagent concentration to a respective modeled TOF of the spatial dependence TOF model by computing a linear combination of the speed of the sound waves in the porous material prior to diffusion with the reagent and the speed of the sound waves in the reagent being free of the porous material; and selecting a next one of the candidate diffusivity constants and repeating this step and the three previous steps for the next selected candidate diffusivity constant until a termination criterion is reached.

Embodiment 7

The method of embodiment 6, wherein the speed of sound waves in the reagent is calculated by transmitting an ultrasonic wave between an ultrasonic transmitter and an ultrasonic receiver through the fluid, calculating the TOF between the transmitter and receiver, and calculating the speed of the sound wave of the reagent according to the following formula:

$$r_{fluid} = \frac{d}{t}$$

wherein $r_{fluid}$ is the speed of sound in the reagent, d is the distance between the transmitter and receiver, and t is the TOF between the transmitter and receiver.

Embodiment 8

The method of embodiment 6 or 7, wherein the speed of the sound wafes in the undiffused porous material ($r_{orig}$) is determined according to the following formula:

$$\frac{1}{r_{orig}} = \frac{1}{r_{fluid}} + \frac{\Delta t}{d_{mat}}$$

wherein $\Delta t$ is the difference in TOF between waves passing through the reagent and the porous material and waves passing through the reagent only, and $d_{mat}$ is the thickness of the porous material.

Embodiment 9

The method of any of any one of embodiments 2-8, wherein the spatial dependence concentration model is configured to calculate the expected concentration of the reagent at the candidate diffusivity point by using a heat equation, the heat equation being descriptive of the distribution of heat in a given region of an object having the same 3D shape as the porous material over time.

Embodiment 10

The method of embodiment 9, wherein the porous material is cylindrical and the heat equation is specified by the following formula:

$$c_{fluid}(t, D, x) = c_{max}\left(1 - 2\sum_{n=1}^{\infty} \frac{e^{-D\alpha_n^2 t/R_0^2} J_0(\alpha_n x/R_o)}{\alpha_n J_1(\alpha_n)}\right)$$

wherein $c_{fluid}$ is the expected concentration of the reagent, t is the diffusion time at the selected time point, D is the candidate diffusivity constant, x is the spatial coordinate of the candidate diffusivity point in the depth direction of the porous material, $R_o$ is the radius of the porous material, $J_o$ is a Bessel function of the first kind and $0^{th}$ order, $J_1$ is a Bessel function of the first kind and $1^{st}$ order, $\alpha_n$ is the location of the $n^{th}$ root of a $0^{th}$ order Bessel function, and $c_{max}$ is the maximum concentration of the reagent.

Embodiment 11

The method of any one of embodiments 2-10, the using of the spatial dependence concentration model for computing the spatial dependence TOF model comprising: using a heat equation of an object having the same 3D shape as the porous material for computing, for each unique combination of a time point, a candidate diffusivity constant and a candidate diffusivity point, a respective expected reagent concentration ($c_{fluid}$); computing, from all expected reagent concentration ($c_{fluid}$) computed for a particular time point, an integrated expected reagent concentration ($c_{determined}$) by integrating the expected reagent concentrations ($c_{fluid}$) of said time point spatially over the radius of the porous material; converting each of the integrated expected reagent concentrations ($c_{determined}$) into a respective one of the modeled TOFs of the spatial dependence TOF model.

Embodiment 12

The method of embodiment 11, the computing of the integrated expected reagent concentration ($c_{determined}$) being performed according to the following formula:

$$c_{detected}(t) = \frac{2}{R_o}\int_0^{R_o} c_{fluid}(t, x)dx$$

wherein $c_{fluid}$ is the expected concentration of the reagent, t is the diffusion time at the selected time point, $c_{detected}$ is the integrated expected reagent concentration, x is the spatial coordinate of the candidate diffusivity point in the depth direction of the porous material, and $R_o$ is the radius of the porous material.

Embodiment 13

The method of embodiment 11 or 12, wherein the converting of each of the integrated expected reagent concentrations ($c_{determined}$) into a respective one of the modeled TOFs of the spatial dependence TOF model is computed according to the following formula:

$$TOF_{simulated}(t, D) = \frac{d_{mat}}{r_{orig}(t=0) + \rho c_{detecdted}(t)(r_{orig}(t=0) - r_{fluid})}$$

wherein TOF is one of the modeled TOF values of the spatial dependency TOF model resulting from the conversion, $r_{orig}$ is the speed of the sound wave in the porous material being free of the reagent, $r_{fluid}$ is the speed of the sound wave in the reagent being free of the porous material, $c_{determined}$ is the integrated expected reagent concentration, D is the candidate diffusivity constant, t is the diffusion time at the selected time point, and $\rho$ is the volume porosity of the porous material and wherein $d_{mat}$ is the thickness of the porous material.

Embodiment 14

The method of any one of embodiments 2-13, wherein the error function is calculated according to the following formula:

$$\text{Error}(D) = \frac{1}{N}\sum_{t=1}^{N}(TOF_{simulated}(t, D) - TOF_{experimental}(t))^2.$$

Embodiment 15

The method of any one of embodiments 2-14, further comprising:
analyzing a plurality of the modeled TOFs of the spatial dependence TOF model relating to a particular candidate diffusivity point and to a particular candidate diffusivity constants and having been modeled for different time points, the analysis being performed for identifying an expected decay constant ($\tau_{simulated}$), the expected decay constant indicating a time span after which the modeled TOFs have decayed by a predefined percentage; analyzing a plurality of the measured TOFs of the spatial dependence TOF model relating to the particular candidate diffusivity point and to the particular candidate diffusivity constants and having been measured at the different time points, the analysis being performed for identifying an experimental decay constant ($\tau_{experimental}$), the experimental decay constant indicating a time span after which the experimental TOFs have decayed by a predefined percentage; wherein the error function is calculated according to the following formula:

$$\text{Error}(D) = (\tau_{simulated}(D) - \tau_{experimental})^2$$

wherein D is the candidate diffusivity constant.

Embodiment 16

The method according to any one of embodiments 2-15 being performed by a processor of a computer system communicatively coupled to the acoustic monitoring device.

Embodiment 17

The method according to any one of embodiments 2-16 comprising:
acquiring a reference time, the reference time indicating a time of sufficient diffusion of the porous material with the reagent; calculating a sufficient diffusion time from the output diffusivity constant; and leaving the tissue sample immersed in the fixative for at least the calculated sufficient diffusion time.

Embodiment 18

The method of any one of embodiments 2-17, the reagent being a liquid, the plurality of time points respectively indicating the time having lapsed since the porous material was immersed into a volume of the liquid.

Embodiment 19

The method of any one of embodiments 2-18, the reagent being a fixation solution and/or the porous material being a tissue sample.

Embodiment 20

The method of any one of embodiments 2-19, further comprising: immersing the porous material in the reagent; keeping the immersed porous material at a temperature from 0° C. to 15° C. while the acoustic waves are detected; for each of the plurality of time points, comparing the experimental TOF with a reference TOF, wherein the reference TOF indicates that the tissue sample is sufficiently diffused with the reagent; in case the experimental TOF reaches the threshold, allowing the temperature of the tissue sample and the reagent to rise to the ambient temperature or triggering the heating of the temperature of the tissue sample and the reagent to a temperature of more than 20° C.

Embodiment 21

The method of any one of embodiments 2-19, further comprising:
fixing the tissue sample to obtain a fixed tissue sample; contacting the fixed tissue sample with a specific binding entity capable of binding to the labile biomarker; and detecting binding of the specific binding entity.

Embodiment 22

A tangible non-transitory computer-readable medium to store computer-readable code that is executed by a processor to perform the method according to any one of embodiments 2-16.

Embodiment 23

A method for determining a true diffusivity constant for a sample immersed within a reagent, the method comprising: simulating a spatial dependence of a diffusion into the sample over a plurality of time points and for each of a plurality of candidate diffusivity constants to generate a model time-of-flight; and comparing the model time-of-flight with an experimental time-of-flight to obtain an error function; wherein a minimum of the error function yields the true diffusivity constant.

Embodiment 24

The method of embodiment 23, wherein the plurality of candidate diffusivity constants comprises a range of candidate diffusivity constants provided by an external source.

Embodiment 25

The method of any one of embodiments 23-24, further comprising determining an absolute acoustic velocity for the sample.

Embodiment 26

The method of embodiment 25, wherein determining the acoustic velocity comprises calculating the speed of sound in the reagent, and determining the thickness of the sample.

Embodiment 27

The method of any one of embodiments 23-26, wherein simulating the spatial dependence further comprises determining a model concentration of the reagent through the sample over the plurality of time points.

Embodiment 28

The method of embodiment 27, wherein simulating the spatial dependence further comprises determining a concentration of the reagent as a function of time and space using the solution to a heat equation for the sample.

Embodiment 29

The method of embodiment 28, wherein the solution to the heat equation for the sample is based on a geometry of the sample.

Embodiment 30

The method of any one of embodiments 27-29, wherein simulating the spatial dependence further comprises converting the model concentration into a time-of-flight.

Embodiment 31

The method of embodiment 30, wherein the model time-of-flight is obtained by determining a time-of-flights for each of the plurality of candidate diffusivity constants.

Embodiment 32

The method of any one of embodiments 23-31, wherein the error function is based on a point-by-point difference between the model time-of-flight and the experimental time-of-flight.

Embodiment 33

The method of any one of embodiments 23-32, wherein the error function is based on a rate of diffusion between the model time-of-flight and the experimental time-of-flight.

Embodiment 34

The method of any one of embodiments 23-33, further comprising determining an error between an experimental and simulated time-of-flight for each candidate diffusivity constant.

Embodiment 35

The method of embodiment 34, wherein the error function is based on the error.

Embodiment 36

A system comprising: an acoustic monitoring device that detects acoustic waves that have traveled through a tissue sample; and a computing device communicatively coupled to the acoustic monitoring device, the computing device is configured to evaluate a speed of the acoustic waves based on a time of flight and including instructions, when executed, for causing the processing system to perform operations comprising: setting a range of candidate diffusivity constants for the tissue sample; simulating a spatial dependence of a reagent within the tissue sample for a plurality of time points and for a first of the range of candidate diffusivity points; determining a modeled time-of-flight based on the spatial dependence; repeating the spatial dependence simulation for each of the plurality of diffusivity constants; and determining an error between the modeled-time-of-flight for the plurality of diffusivity constants versus an experimental time-of-flight for the tissue sample;
wherein a minimum of an error function based on the error yields a true diffusivity constant for the tissue sample.

Embodiment 37

The system of embodiment 36, wherein the operations further comprise solving a heat equation for the tissue sample to determine the modeled time-of-flight.

Embodiment 38

The system of embodiment 36 or 37, wherein the error is determined for each candidate diffusivity constant.

Embodiment 39

The system of embodiment 37, wherein the error function is determined from the error for each diffusivity constant as a function of the diffusivity constant.

Embodiment 40

A tangible non-transitory computer-readable medium to store computer-readable code that is executed by a processor to perform operations comprising: comparing a simulated time-of-flight for a sample material with an experimental time-of-flight for the sample material; and obtaining a diffusivity constant for the sample material based on a minimum of an error function between the simulated time-of-flight and the acoustic time-of-flight.

Embodiment 41

A method of determining a diffusivity constant of a fluid diffusing into a porous material, said method comprising: immersing a sample of the porous material into a volume of the fluid; collecting a set of acoustic data for the sample of the porous material immersed in the volume of the fluid with an acoustic monitoring system and transmitting said acoustic data set to a signal analyzer, said acoustic data set comprising: (b1) absolute sound velocity of ultrasonic waves in the porous material prior to diffusion with fluid; (b2) TOF of ultrasonic waves through the porous material at least at one time point during diffusion of fluid into the porous material ($TOF_{experimental}$); (b3) absolute sound velocity of ultrasonic waves in the fluid; and (b4) a thickness of the porous material; (c) calculating a diffusivity constant for diffusion of the fluid into the porous material on a signal analyzer by: (c1) modeling a TOF trend for each of a plurality of candidate diffusivity constants by: (c1a) selecting a first candidate diffusivity constant; (c1b) selecting a plurality of diffusion times corresponding to the time points of (b2); (c1c) calculating a concentration of the fluid at each of a plurality of depths through thickness (b4) of the porous sample as a function of time and space; (c1d) calculating a total amount of diffused reagent at each time point ($c_{detected}$) (c1e) calculating an expected TOF differential resulting from the concentration determined in (c1d) as a linear combination of (b1) and (b3); and (c1f) repeating (c1a)-(c1e) for a plurality of candidate diffusivity constants; (c2) calculating an error function between the TOF of (b2) and each of the TOF differentials calculated from (c1) as a function of diffusivity constant, wherein the true diffusivity constant is a minimum of the error function.

Embodiment 42

The method of embodiment 41, wherein the speed of sound in the fluid is calculated by transmitting an ultrasonic wave between an ultrasonic transmitter and an ultrasonic receiver through the fluid, calculating the time of flight between the transmitter and receiver, and calculating the speed of sound according to the following formula:

$$r_{fluid} = \frac{d}{t}$$

wherein $r_{fluid}$ is the speed of sound in the fluid, d is the distance between the transmitter and receiver, and t is the time of flight (TOF) between the transmitter and receiver.

Embodiment 43

The method of embodiment 42, wherein the speed of sound in the undiffused porous material ($r_{orig}$) is determined according to the following formula:

$$\frac{1}{r_{orig}} = \frac{1}{r_{fluid}} + \frac{\Delta t}{d_{mat}}$$

wherein $\Delta t$ is the difference in TOF between waves passing through the fluid and the porous material and waves passing through the fluid only, and $d_{mat}$ is the thickness of the porous material.

Embodiment 44

The method of any of embodiments 41-43, wherein the thickness of the porous material is determined using a pulse echo ultrasound.

Embodiment 45

The method of any of embodiments 41-44, wherein the porous material is cylindrical and the concentration of the fluid at each of the plurality of depths through thickness (b4) of the porous sample is calculated according to the following formula:

$$c_{fluid}(t, D, x) = c_{max}\left(1 - 2\sum_{n=1}^{\infty} \frac{e^{-D\alpha_n^2 t/R_0^2} J_0(\alpha_n x/R_o)}{\alpha_n J_1(\alpha_n)}\right)$$

wherein $c_{fluid}$ is the concentration, t is the diffusion time at the selected time point, D is the candidate diffusivity constant, x is the spatial coordinate in the depth direction of the tissue, $R_o$ is the radius of the sample, $J_o$ is a Bessel function of the first kind and $0^{th}$ order, $J_1$ is a Bessel function of the first kind and $1^{st}$ order, $\alpha_n$ is the location of the $n^{th}$ root of a $0^{th}$ order Bessel function, and $c_{max}$ is the maximum concentration of the reagent.

Embodiment 46

The method of embodiment 45, wherein the total amount of diffused reagent ($c_{detected}$) is calculated according to the following formula:

$$c_{detected}(t) = \frac{2}{R_o}\int_0^{R_o} c_{fluid}(t, x) dx$$

Embodiment 47

The method of embodiment 46, wherein the expected TOF differential is calculated according to the following formula:

$$TOF_{simulated}(t, D) = \frac{d_{mat}}{r_{orig}(t=0) + \rho c_{detected}(t)(r_{orig}(t=0) - r_{fluid})}$$

wherein $d_{mat}$ is the thickness of the material and $\rho$ is porosity of the material.

Embodiment 48

The method of embodiment 47, wherein the error function is calculated according to the following formula:

$$\text{Error}(D) = \frac{1}{N}\sum_{t=1}^{N}(TOF_{simulated}(t, D) - TOF_{experimental}(t))^2.$$

Embodiment 49

The method of any of embodiments 41-48, wherein said porous material is a tissue sample and the fluid is a fixative solution.

Embodiment 50

A method of fixing a tissue sample, said method comprising calculating a diffusivity constant of a tissue sample immersed in a fixative solution according to a method of embodiment 49, calculating a sufficient diffusion time based upon the calculated diffusivity constant, and leaving the tissue sample immersed in the fixative for at least the calculated sufficient diffusion time.

Embodiment 51

A method of fixing a tissue sample, said method comprising: obtaining a tissue sample sufficiently diffused with a cross-linking fixative solution by: (a1) immersing an unfixed tissue sample freshly obtained from a subject into a volume of the cross-linking fixative solution, wherein the cross-linking fixative is at a temperature from 0° C. to 15° C.; (a2) calculating a diffusivity constant according to a method of embodiment 28; and (a3) determining a sufficient diffusion time based on the calculated diffusivity constant; (b) after the tissue sample has been immersed in the cross-linking fixative solution for the sufficient diffusion time, raising the temperature of the tissue sample to a temperature in the range of room temperature to 50° C., and holding the tissue sample in said range of temperatures for a period of time sufficient to allow fixation of the tissue sample.

Embodiment 52

A method of detecting a labile biomarker in a tissue sample, said method comprising: fixing the tissue sample according to the method of embodiment 30 to obtain a fixed tissue sample; contacting the fixed tissue sample with a specific binding entity capable of binding to the labile biomarker; and detecting binding of the specific binding entity.

Embodiment 53

The method of embodiment 52, wherein the labile biomarker is selected from the group consisting of a phosphorylated protein, an mRNA, and a miRNA.

The foregoing disclosure of the exemplary embodiments of the present subject disclosure has been presented for purposes of illustration and description. It is not intended to be exhaustive or to limit the subject disclosure to the precise forms disclosed. Many variations and modifications of the embodiments described herein will be apparent to one of ordinary skill in the art in light of the above disclosure.

Further, in describing representative embodiments of the present subject disclosure, the specification may have presented the method and/or process of the present subject disclosure as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present subject disclosure should not be limited to the performance of their steps in the order written, and one skilled in the art can readily appreciate that the sequences may be varied and still remain within the spirit and scope of the present subject disclosure.

The invention claimed is:

1. A method for determining a true diffusivity constant of a porous material comprising:

computing a set of experimental time-of-flights (TOFs) from measured acoustic data of acoustic waves, the acoustic waves having been detected by an acoustic monitoring device and having traveled through the porous material, each experimental TOF of the computed set of experimental TOFs indicating the TOF of acoustic waves that traveled through a candidate diffusivity point of the porous material at a respective one of a plurality of time points;

setting a range of candidate diffusivity constants for the porous material;

for each of the candidate diffusivity constants, simulating a spatial dependence concentration model of an expected concentration of a reagent within the porous material for the plurality of time points and for the candidate diffusivity point, the expected concentration of the reagent being a function of time, space and said candidate diffusivity constant;

using the simulated spatial dependence concentration model for computing a spatial dependence TOF model for the porous material, the TOF model assigning, to the candidate diffusivity point for each of the plurality of time points and for each of the candidate diffusivity constants, a respectively modeled TOF; and determining an error function for the candidate diffusivity point for each of the plurality of time points and for each of the candidate diffusivity constants, the error function being indicative of a distance between each of the modeled TOFs assigned to said candidate diffusivity point from a corresponding experimental TOF, the experimental TOF having been measured by the acoustic monitoring device at the same time point as used for modeling its corresponding modeled TOF;

determining a minimum error function based on the determined error function for the candidate diffusivity point for each of the plurality of time points and for each of the candidate diffusivity constants;

calculating the true diffusivity constant for the porous material based on the determined minimum error function, wherein the computation of the spatial dependence TOF model comprising:

selecting a first one of the candidate diffusivity constants;

calculating an expected reagent concentration ($c_{reagent}$) at each of the candidate diffusivity points in the porous material for each of the plurality of time points in dependence of the selected candidate diffusivity constant;

calculating an integrated reagent concentration ($c_{detected}$) for each of the plurality of time points and for each of the candidate diffusivity constants by integrating the expected reagent concentration ($c_{reagent}$) calculated for said time point and said candidate diffusivity constant over a radius of the porous material;

converting the integrated reagent concentration to the respective modeled TOF of the spatial dependence TOF model by computing a linear combination of a speed of the acoustic waves in the porous material prior to diffusion with the reagent and the speed of the acoustic waves in the reagent being free of the porous material; and selecting a next one of the candidate diffusivity constants and repeating this step and the three previous steps for the next selected candidate diffusivity constant until a termination criterion is reached.

2. The method of claim 1, wherein computing the spatial dependence TOF model comprises determining each of the modeled TOFs by solving a heat equation for the porous material.

3. The method of claim 1, wherein the acoustic data comprises:

velocity of the acoustic waves in the porous material prior to diffusion with the reagent; and/or the experimental TOFs of the acoustic waves through the porous material at the plurality of time points during diffusion of the reagent into the porous material; and/or experimental phase shift data for computing the experimental TOFs from the experimental phase shift data;

velocity of the acoustic waves in the reagent being free of the porous material; and/or a thickness of the porous material.

4. The method of claim 1, wherein the speed of the acoustic waves in the reagent being free of the porous material is calculated by transmitting an ultrasonic wave between an ultrasonic transmitter and an ultrasonic receiver through the fluid, calculating the TOF between the ultrasonic transmitter and the ultrasonic receiver, and calculating the speed of the acoustic wave of the reagent according to the following formula:

$$r_{fluid} = \frac{d}{t}$$

wherein $r_{fluid}$ is the speed of sound in the reagent, d is a distance between the ultrasonic transmitter and the ultrasonic receiver, and t is the TOF between the transmitter and receiver.

5. The method of claim 1, wherein the speed of the acoustic waves in the undiffused porous material ($r_{orig}$) are determined according to the following formula:

$$\frac{1}{r_{orig}} = \frac{1}{r_{fluid}} + \frac{\Delta t}{d_{mat}}$$

wherein $\Delta t$ is a difference in TOF between waves passing through the reagent and the porous material and waves passing through the reagent only, and $d_{mat}$ is a thickness of the porous material.

6. The method of claim 1, wherein the spatial dependence concentration model is configured to calculate the expected concentration of the reagent at the candidate diffusivity point by using a heat equation, the heat equation being descriptive of the distribution of heat in a given region of an object having a same 3D shape as the porous material over time.

7. The method of claim 6, wherein the porous material is cylindrical and the heat equation is specified by the following formula:

$$c_{fluid}(t, D, x) = c_{max}\left(1 - 2\sum_{n=1}^{\infty} \frac{e^{-D\alpha_n^2 t/R_0^2} J_0(\alpha_n x/R_o)}{\alpha_n J_1(\alpha_n)}\right)$$

wherein $c_{fluid}$ is the expected concentration of the reagent, t is the diffusion time at the selected time point, D is the candidate diffusivity constant, x is the spatial coordinate of the candidate diffusivity point in a depth direction of the porous material, $R_o$ is a radius of the porous material, $J_o$ is a Bessel function of the first kind and $0^{th}$ order, $J_1$ is a Bessel function of the first kind and $1^{st}$ order, $\alpha_n$ is the location of the $n^{th}$ root of a $0^{th}$ order Bessel function, and $c_{max}$ is the maximum concentration of the reagent.

8. The method of claim 1, wherein the error function is calculated according to the following formula:

$$\text{Error}(D) = \frac{1}{N} \sum_{t=1}^{N} (TOF_{simulated}(t, D) - TOF_{experimental}(t))^2$$

wherein D is a candidate diffusivity constant, t is a diffusion time at the selected time point, x is a spatial coordinate in the depth direction of the tissue, $TOF_{simulated}$ is a simulated or expected TOF, $TOF_{experimental}$ is an experimentally determined TOF, and N is a number of experimentally measured TOF signals.

9. The method of claim 1, further comprising:
analyzing a plurality of the modeled TOFs of the spatial dependence TOF model relating to one of the candidate diffusivity points and to one of the candidate diffusivity constants and having been modeled for different time points, the analysis being performed for identifying an expected decay constant ($\tau_{simulated}$), the expected decay constant indicating a time span after which the modeled TOFs have decayed by a predefined percentage;
analyzing a plurality of experimental TOFs of the spatial dependence TOF model relating to the particular candidate diffusivity point and to the particular candidate diffusivity constants and having been measured at the different time points, the analysis being performed for identifying an experimental decay constant ($\tau_{experimental}$), the experimental decay constant indicating a time span after which the experimental TOFs have decayed by a predefined percentage;
wherein the error function is calculated according to the following formula:

$$\text{Error}(D) = (\tau_{simulated}(D) - \tau_{experimental})^2$$

wherein D is the candidate diffusivity constant.

10. The method of claim 1 being performed by a processor of a computer system communicatively coupled to the acoustic monitoring device.

11. The method of claim 1, wherein the reagent comprises a liquid, and wherein the plurality of time points respectively indicating the time having lapsed since the porous material was immersed into a volume of the liquid.

12. The method of claim 1, wherein the reagent comprises a fixation solution and where the porous material comprises a tissue sample.

13. The method of claim 1, further comprising:
immersing the porous material in the reagent;
keeping the immersed porous material at a temperature from 0° C. to 15° C. while the acoustic waves are detected;
for each of the plurality of time points, comparing the experimental TOF with a reference TOF.

14. The method of claim 13, wherein if the experimental TOF reaches a threshold, allowing the temperature of the tissue sample and the reagent to rise to an ambient temperature or triggering heating of the temperature of the tissue sample and the reagent to a temperature of more than 20° C.

15. The method of claim 1, further comprising:
fixing a tissue sample to obtain a fixed tissue sample;
contacting the fixed tissue sample with a specific binding entity capable of binding to a labile biomarker; and
detecting binding of the specific binding entity.

16. A method of determining a diffusivity constant of a fluid diffusing into a porous material, said method comprising:
(a) immersing a sample of the porous material into a volume of the fluid;
(b) collecting a set of acoustic data for the sample of the porous material immersed in the volume of the fluid with an acoustic monitoring system, said acoustic data set comprising:
(b1) a velocity of ultrasonic waves in the porous material prior to diffusion with fluid;
(b2) one or more experimental time-of-flight (TOF) measurements of ultrasonic waves through the porous material, wherein each of the one or more TOF measurements occurs at one time point during diffusion of the fluid into the porous material $TOF_{experimental}$;
(b3) a velocity of ultrasonic waves in the fluid; and
(b4) a thickness of the porous material;
(c) calculating a diffusivity constant for diffusion of the fluid into the porous material based on the collected of acoustic data, wherein the calculating of the diffusivity constant comprises:
(c1) modeling a TOF trend for each of a plurality of candidate diffusivity constants by:
(c1a) selecting a first candidate diffusivity constant;
(c1b) selecting a one or more diffusion times corresponding to the one or more time points of the one or more TOF measurements;
(c1c) calculating a concentration of the fluid at each of a plurality of depths through a thickness (b4) of the porous sample as a function of time and space;
(c1d) calculating a total amount of diffused reagent at each time point ($c_{detected}$)
(c1e) calculating an expected TOF differential resulting from the concentration determined in (c1d) as a linear combination of (b1) and (b3); and
(c1f) repeating (c1a)-(c1e) for a plurality of candidate diffusivity constants;
(c2) calculating an error function between the TOF of (b2) and each of the TOF differentials calculated from (c1) as a function of diffusivity constant, wherein the true diffusivity constant is a minimum of the error function.

17. The method of claim 16, wherein the velocity of the ultrasonic waves in the fluid is calculated by transmitting an ultrasonic wave between an ultrasonic transmitter and an ultrasonic receiver through the fluid, calculating the time of flight between the ultrasonic transmitter and the ultrasonic receiver, and calculating the speed of sound according to the following formula:

$$r_{fluid} = \frac{d}{t}$$

wherein $r_{fluid}$ is the speed of sound in the fluid, d is the distance between the ultrasonic transmitter and the ultrasonic receiver, and t is the time of flight (TOF) between the transmitter and receiver.

18. The method of claim 17, wherein the velocity of the ultrasonic waves of sound in the undiffused porous material ($r_{orig}$) is determined according to the following formula:

$$\frac{1}{r_{orig}} = \frac{1}{r_{fluid}} + \frac{\Delta t}{d_{mat}}$$

wherein $\Delta t$ is the difference in TOF between waves passing through the fluid and the porous material and waves passing through the fluid only, and $d_{mat}$ is the thickness of the porous material.

19. The method of claim 16, wherein the thickness of the porous material is determined using a pulse echo ultrasound.

20. The method of claim 16, wherein the porous material is cylindrical and the concentration of the fluid at each of the plurality of depths through thickness (b4) of the porous sample is calculated according to the following formula:

$$c_{fluid}(t, D, x) = c_{max}\left(1 - 2\sum_{n=1}^{\infty} \frac{e^{-D\alpha_n^2 t/R_0^2} J_0(\alpha_n x/R_o)}{\alpha_n J_1(\alpha_n)}\right)$$

wherein $c_{fluid}$ is the concentration, t is the diffusion time at the selected time point, D is the candidate diffusivity constant, x is the spatial coordinate in the depth direction of the tissue, $R_o$ is the radius of the sample, $J_o$ is a Bessel function of the first kind and $0^{th}$ order, $J_1$ is a Bessel function of the first kind and $1^{st}$ order, $\alpha_n$ is the location of the $n^{th}$ root of a $0^{th}$ order Bessel function, and $c_{max}$ is the maximum concentration of the reagent.

21. The method of claim 20, wherein the total amount of diffused reagent ($c_{detected}$) is calculated according to the following formula:

$$c_{detected}(t) = \frac{2}{R_o}\int_0^{R_o} c_{fluid}(t, x)dx.$$

22. The method of claim 21, wherein the expected TOF differential is calculated according to the following formula:

$$TOF_{simulated}(t, D) = \frac{d_{mat}}{r_{orig}(t=0) + \rho c_{detected}(t)(r_{orig}(t=0) - r_{fluid})}$$

wherein $d_{mat}$ at is the thickness of the material and $\rho$ is porosity of the material.

23. The method of claim 22, wherein the error function is calculated according to the following formula:

$$\text{Error}(D) = \frac{1}{N}\sum_{t=1}^{N}(TOF_{simulated}(t, D) - TOF_{experimental}(t))^2.$$

wherein D is a candidate diffusivity constant, t is a diffusion time at the selected time point, x is a spatial coordinate in the depth direction of the tissue, $TOF_{simulated}$ is a simulated or expected TOF, $TOF_{experimental}$ is an experimentally determined TOF, and N is a number of experimentally measured TOF signals.

24. The method of 16, wherein said porous material is a tissue sample and the fluid is a fixative solution.

25. A method for determining a true diffusivity constant of a porous material comprising:

computing a set of experimental TOFs from measured acoustic data of acoustic waves, the acoustic waves having been detected by an acoustic monitoring device and having traveled through the porous material, each experimental TOF of the computed set of experimental TOFs indicating the TOF of acoustic waves that traveled through a candidate diffusivity point of the porous material at a respective one of a plurality of time points;

setting a range of candidate diffusivity constants for the porous material;

for each of the candidate diffusivity constants, simulating a spatial dependence concentration model of an expected concentration of a reagent within the porous material for the plurality of time points and for the candidate diffusivity point, the expected concentration of the reagent being a function of time, space and said candidate diffusivity constant;

using the simulated spatial dependence concentration model for computing a spatial dependence TOF model for the porous material, the TOF model assigning, to the candidate diffusivity point for each of the plurality of time points and for each of the candidate diffusivity constants, a respectively modeled TOF; and determining an error function for the candidate diffusivity point for each of the plurality of time points and for each of the candidate diffusivity constants, the error function being indicative of a distance between each of the modeled TOFs assigned to said candidate diffusivity point from a corresponding experimental TOF, the experimental TOF having been measured by the acoustic monitoring device at the same time point as used for modeling its corresponding modeled TOF;

determining a minimum error function based on the determined error function for the candidate diffusivity point for each of the plurality of time points and for each of the candidate diffusivity constants;

calculating the true diffusivity constant for the porous material based on the determined minimum error function, wherein the using of the spatial dependence concentration model for computing the spatial dependence TOF model comprises:

using a heat equation of an object having the same 3D shape as the porous material for computing, for each unique combination of a time point, a candidate diffusivity constant and a candidate diffusivity point, a respective expected reagent concentration ($c_{fluid}$);

computing, from all expected reagent concentration ($c_{fluid}$) computed for a particular time point, an integrated expected reagent concentration ($c_{determined}$) by integrating the expected reagent concentrations ($c_{fluid}$) of said time point spatially over a radius of the porous material;

converting each of the integrated expected reagent concentrations ($c_{determined}$) into the respective one of the modeled TOFs of the spatial dependence TOF model.

26. The method of claim 25, wherein the computing of the integrated expected reagent concentration ($c_{determmed}$) being performed according to the following formula:

$$c_{detected}(t) = \frac{2}{R_o}\int_0^{R_o} c_{fluid}(t, x)dx$$

wherein $c_{fluid}$ is the expected concentration of the reagent, t is the diffusion time at the selected time point, $c_{detected}$ is the integrated expected reagent concentration, x is the spatial coordinate of the candidate diffusivity point in a depth direction of the porous material, and $R_o$ is a radius of the porous material.

27. The method of claim 25, wherein the converting of each of the integrated expected reagent concentrations ($c_{determined}$) into a respective one of the modeled TOFs of the spatial dependence TOF model is computed according to the following formula:

$$TOF_{simulated}(t, D) = \frac{d_{mat}}{r_{orig}(t=0) + \rho c_{detected}(t)(r_{orig}(t=0) - r_{fluid})}$$

wherein $TOF_{simulated}$ is one of the modeled TOF values of the spatial dependency TOF model resulting from the conversion, $r_{orig}$ is the speed of the sound wave in the porous material being free of the reagent, $r_{fluid}$ is the speed of the sound wave in the reagent being free of the porous material, $c_{determined}$ is the integrated expected reagent concentration, D is the candidate diffusivity constant, t is the diffusion time at the selected time point, and ρ is a volume porosity of the porous material and wherein $d_{mat}$ is a thickness of the porous material.

* * * * *